(12) United States Patent
Ting et al.

(10) Patent No.: US 10,105,704 B2
(45) Date of Patent: Oct. 23, 2018

(54) SYSTEM AND METHOD FOR MICROPLATE PRESSURIZATION

(75) Inventors: Edmund Y. Ting, Kent, WA (US); Alexander Lazarev, Lexington, MA (US)

(73) Assignee: PRESSURE BIOSCIENCES, INC., South Easton, MA (US)

( * ) Notice: Subject to any disclaimer, the term of this patent is extended or adjusted under 35 U.S.C. 154(b) by 583 days.

(21) Appl. No.: 13/282,904

(22) Filed: Oct. 27, 2011

(65) Prior Publication Data

US 2012/0103113 A1  May 3, 2012

Related U.S. Application Data

(60) Provisional application No. 61/407,729, filed on Oct. 28, 2010.

(51) Int. Cl.
| | |
|---|---|
| *B01L 3/00* | (2006.01) |
| *G01N 1/28* | (2006.01) |
| *B01L 9/00* | (2006.01) |

(52) U.S. Cl.
CPC ........... *B01L 3/50853* (2013.01); *G01N 1/28* (2013.01); *B01L 3/50851* (2013.01); *B01L 9/50* (2013.01); *B01L 2200/021* (2013.01); *B01L 2200/0631* (2013.01); *B01L 2200/0678* (2013.01); *B01L 2200/0689* (2013.01); *B01L 2200/141* (2013.01); *B01L 2300/042* (2013.01); *B01L 2300/048* (2013.01); *B01L 2300/123* (2013.01); *B01L 2300/14* (2013.01); *B01L 2400/0487* (2013.01)

(58) Field of Classification Search
CPC ............... B01J 19/0046; B01J 19/0093; B01L 3/50853; B01L 2300/123; B01L 2300/14

USPC ....... 422/129, 130, 547, 551, 552, 553, 565, 422/568

See application file for complete search history.

(56) References Cited

U.S. PATENT DOCUMENTS

| | | | |
|---|---|---|---|
| 5,342,581 A | 8/1994 | Sanadi | |
| 5,604,130 A | 2/1997 | Warner et al. | |
| 6,036,923 A | 3/2000 | Laugharn, Jr. et al. | |
| 6,556,940 B1 * | 4/2003 | Tretiakov et al. | 702/130 |
| 6,635,469 B1 | 10/2003 | Litt et al. | |
| 7,018,589 B1 * | 3/2006 | Erden et al. | 422/130 |
| 7,064,192 B2 | 6/2006 | Randolph et al. | |
| 2002/0137157 A1 | 9/2002 | Randolph et al. | |
| 2003/0083475 A1 | 5/2003 | Randolph et al. | |

(Continued)

FOREIGN PATENT DOCUMENTS

EP  0814900 B1  9/2001

OTHER PUBLICATIONS

International Search Report for PCT/US2011/058062 dated Mar. 5, 2012.

*Primary Examiner* — Jill A Warden
*Assistant Examiner* — Dwayne K Handy
(74) *Attorney, Agent, or Firm* — Lando & Anastasi, LLP

(57) ABSTRACT

A pressurizable sample system includes a microplate having a planar plate surface and several sample wells. Each sample well has a flange positioned circumferentially around an outer surface of the sample well and against the planar plate surface. The sample system further includes a capping plate with a planar cap surface and several caps projecting from the planar cap surface. Each cap has a geometrical configuration in complementary correspondence with the configuration of the sample well.

17 Claims, 7 Drawing Sheets

(56) References Cited

U.S. PATENT DOCUMENTS

| | | | |
|---|---|---|---|
| 2003/0161763 A1* | 8/2003 | Erden | B01J 3/04 |
| | | | 422/130 |
| 2004/0038333 A1 | 2/2004 | Randolph et al. | |
| 2004/0151641 A1* | 8/2004 | Van Erden | B01J 3/04 |
| | | | 506/37 |
| 2004/0223885 A1 | 11/2004 | Keen et al. | |
| 2005/0226779 A1 | 10/2005 | Oldham et al. | |
| 2006/0188970 A1 | 8/2006 | Randolph et al. | |
| 2007/0154361 A1 | 7/2007 | Van Erden et al. | |
| 2008/0300386 A1 | 12/2008 | Lazarev et al. | |
| 2009/0004754 A1 | 1/2009 | Oldenburg | |
| 2009/0197277 A1 | 8/2009 | Beard et al. | |
| 2009/0203068 A1 | 8/2009 | Lopez-Ferrer | |

* cited by examiner

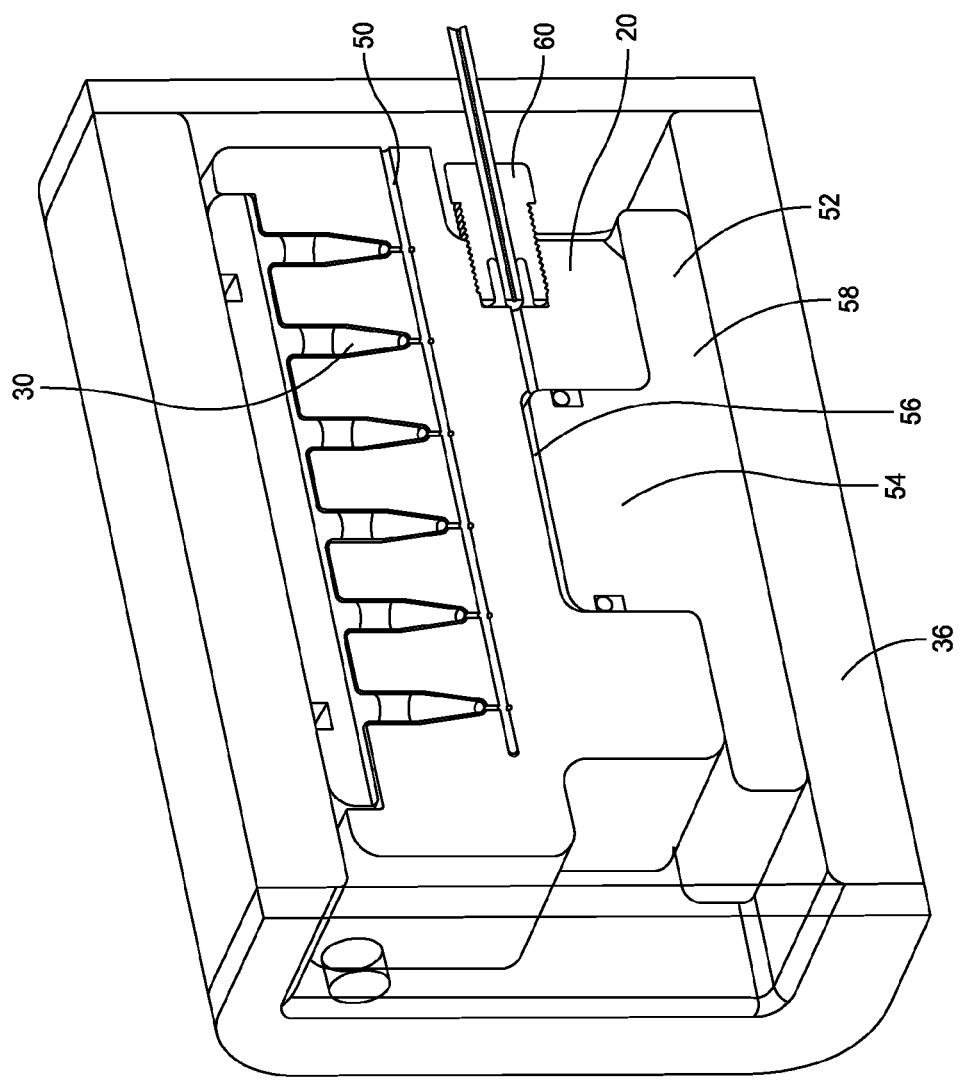

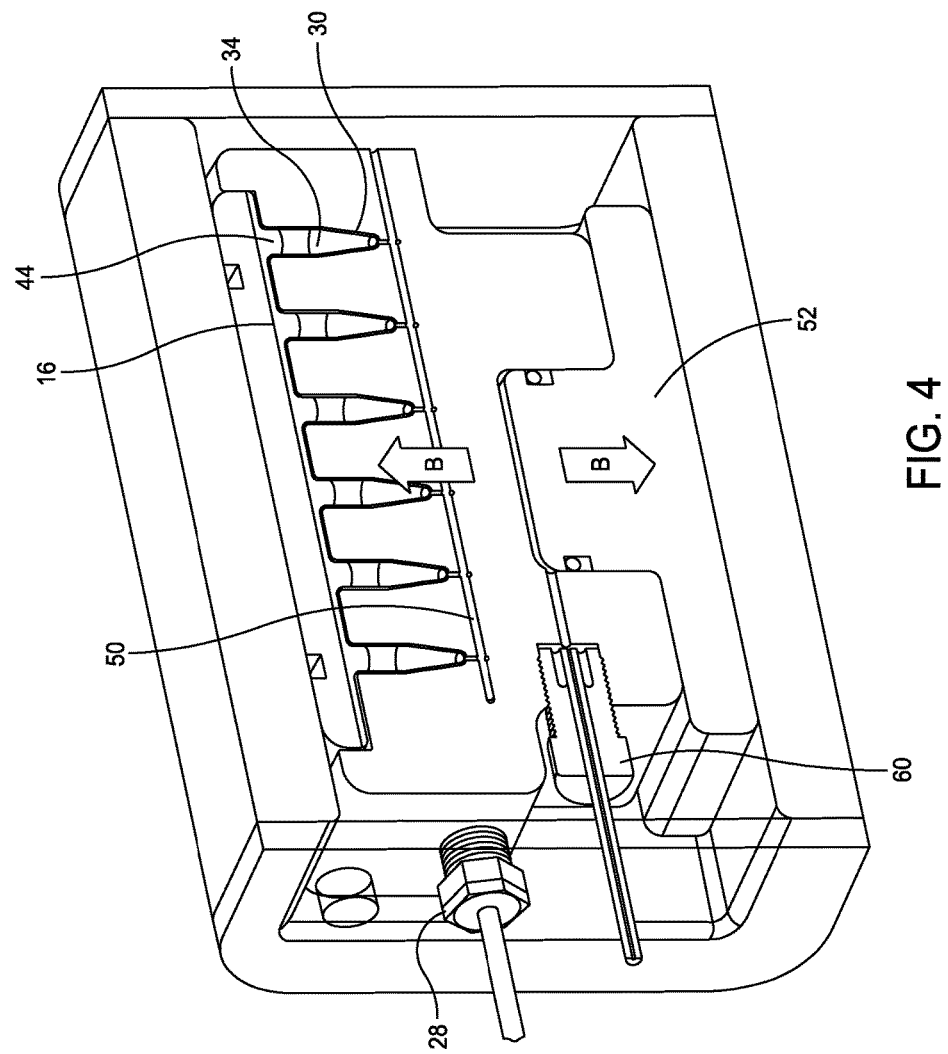

SYSTEM AND METHOD FOR MICROPLATE PRESSURIZATION

CROSS-REFERENCE TO RELATED APPLICATIONS

This application claims priority under 35 U.S.C. § 119(e) to U.S. Provisional Application Ser. No. 61/407,729 entitled "SYSTEM AND METHOD FOR MICROPLATE PRESSURIZATION," filed on Oct. 28, 2010, which is incorporated herein by reference in its entirety.

BACKGROUND OF THE INVENTION

1. Field of Disclosure

This disclosure relates to systems and methods of preparing a sample and, in particular, to systems and methods of pressurizing a sample or group of samples in an inter-well format compatible with the life science industry's standard 4.5 or 9 millimeter (mm) microplate to prepare the sample for further analytical procedures.

2. Discussion of Related Art

Advancements in chemical and biological analysis have been driven by analytical and separation equipment. However, the first step in analytical processes, sample preparation, has received little attention and has predominantly focused on off-line traditional mechanical shearing or chemical approaches at various temperatures. Most analytical instruments require true solutions of the analytes as an input, while most samples, particularly biological and environmental samples, contain cells, tissues, suspensions, emulsions and other heterogeneous compositions. The majority of published methods combine modern state-of-the-art high sensitivity and high resolution analytical methods with the legacy sample preparation steps. Most sample preparation protocols commonly used have been developed before modern molecular analysis methods, such as mass spectrometry, DNA sequencing and PCR amplification techniques, existed. Many sample preparation methods in common use continue to rely on traditional techniques such as mechanical homogenization, ultrasonic cavitational disruption, grinding of frozen samples in liquid nitrogen, etc. Most of these techniques require processing samples one-by-one in a dedicated container, leading to the necessity of manual sample handling or the use of robotic liquid handlers. Sample transfer typically presents a risk of undesired sample loss, potential for operator error, sample cross-contamination, and overall lack of an automated in-line process from initial sample to results.

Thermodynamic control of molecular interactions and chemical equilibria could be accomplished by varying the two orthogonal parameters of temperature and pressure. Temperature has been by far the most widely used perturbation in biochemical thermodynamics. However, a complete thermodynamic response can be utilized by using pressure perturbations, which is governed by different thermodynamic effects than temperature.

Hydrostatic pressure has been used to promote cell lysis, extraction and partitioning of various molecular entities as exemplarily illustrated by Lazarev et al. in U.S. Patent Application Publication No. 2008/0300386 A1, which is incorporated herein by reference in its entirety for all purposes. The control of molecular interactions has also been disclosed as noted by Litt et al. in U.S. Pat. No. 6,635,469 B1, which is also incorporated herein by reference in its entirety for all purposes. Enzymatic reactions, including proteolysis for preanalytical sample preparation in mass spectrometry-based proteomics have also been disclosed by, for example, Laugharn et al. in European Patent Specification No. EP 0 814 900 B1, which is incorporated herein by reference in its entirety for all purposes, and by Lopez-Ferrer in U.S. Patent Application Publication No. 2009/0203068 A1. To date, the application of hydrostatic pressure to liquid samples has been predominantly achieved by pressurizing sample contained in closed pressure vessels. Such techniques may not be practical for pressurization of very small volume liquid samples in the micro liter range and does not interface well with automated analysis systems.

High pressure reactor apparatus have been described by Laugharn et al. in U.S. Pat. No. 6,036,923, which is incorporated herein by reference in its entirety for all purposes, which allows loading and unloading operations to be automated by the use of the high-pressure valves to trap the sample in a segment of the tubular flow path, enabling a variety of applications, ranging from chromatography at high pressure to control of enzyme kinetics under pressure. The design of the reactor described above may not accommodate miniaturization and the volumes of samples which could be pressurized has remained relatively large (1 ml and above). An alternative method of pressurization of small samples has also been described by, for example, Lopez-Ferrer in U.S. Patent Application Publication No. 2009/0203068 A1. Such approach may, however, be limited because the sample material is typically placed in direct contact with the liquid used as a source of hydrostatic pressure through the series of valves, which poses a risk of sample cross-contamination when processing of samples is conducted in a serial fashion. Furthermore such approach can only be pressurized to the maximum pressure level available on the analytical system and the sample pressure cannot be easily controlled to slowly ramp or rapidly cycle pressure as a function of time.

These effects are typically implemented at pressures of between 10,000 psi and 100,000 psi. Currently most analytical instruments used to characterize, identify, or handle biological samples utilize a standard microplate, e.g., a MICROTITER plate, with a 9 mm offset between sample wells. The sample wells are typically arranged in an array of 8×12. The present disclosure provides laboratory apparatus which can subject samples contained in microplates to high pressure to facilitate efforts in many branches of biology ranging from research, quality control, and process enhancement.

The standard microtiter plate is typically 120 mm×85 mm in size. To put this plate into a pressure chamber, the pressure chamber will have to be at least approximately 85 mm in diameter, even if the well depth was 0 mm. In reality, the diameter of any pressure vessel intending to hold a microplate will be about 100 mm in diameter, and at least about 120 mm in length. A pressure vessel of this size will be costly as well as large and heavy due to the high pressure that it must withstand.

BRIEF SUMMARY OF THE INVENTION

One or more aspects of the disclosure can be directed to a pressurizable sample system. In one or more embodiments directed to one or more aspects of the disclosure, the pressurizable sample system can comprise a microplate having a planar plate surface and at least one sample well, the at least one sample well having a flange positioned circumferentially around an outer surface of the at least one well and against the planar plate surface; and a capping plate with a planar cap surface and at least one cap projecting from the planar cap surface, the at least one cap having a geometrical configuration in complementary correspondence with the configuration of the at least one sample well. In one or more embodiments directed to one or more aspects of the disclosure, the pressurizable sample system can also comprise a loading plate configured to contact and distribute an applied pressure across the capping plate.

One or more aspects of the disclosure can be directed to an apparatus for pressurizing a sample. The apparatus for pressurizing a sample can comprise a carrier body having at least one pressurizing fluid port, at least one fluid channel fluidly connected to the at least one pressurizing fluid port, and at least one pressure cell fluidly connectable to the at least one pressurizing fluid port through the at least one channel, the at least one pressure cell defined by a cell cavity with an open end at a receiving surface of the carrier body, the at least one pressure cell having a retaining flange positioned circumferentially around the open end of the cell cavity at the receiving surface of the carrier body; and a casing or yoke having an inner cavity sized and configured to receive the carrier body. In one or more embodiments pertinent to one or more aspects of the disclosure, the apparatus for pressurizing a sample can also comprise a pressure generator fluidly connected to provide a pressurizing fluid into the cell cavity through the at least one pressurizing fluid port. In one or more embodiments pertinent to one or more aspects of the disclosure, the apparatus for pressurizing a sample can also comprise a microplate having planar surface and at least one sample well at least partially defined by a sample well wall open at an end at the planar surface, the at least one sample well sized to be at least partially contained within the at least one cell cavity. In one or more embodiments pertinent to one or more aspects of the disclosure, the at least one sample well can have a sealing flange circumferentially surrounding an outer perimeter of the sample well wall, at least a portion of the sealing flange contiguous with at least a portion of the planar surface of the microplate. In one or more embodiments pertinent to one or more aspects of the disclosure, the sealing flange can have a geometrical configuration corresponding with an inner geometrical configuration of the retaining flange. In one or more embodiments pertinent to one or more aspects of the disclosure, the apparatus for pressurizing a sample can also comprise a capping plate with a planar cap surface and at least one cap projecting from the planar cap surface, the at least one cap having a geometrical configuration in complementary correspondence with an inner configuration of capping section of the at least one sample well. In one or more embodiments pertinent to one or more aspects of the disclosure, the apparatus for pressurizing a sample can further comprise a loading plate configured to contact and distribute an applied pressure onto the capping plate. In one or more embodiments pertinent to one or more aspects of the disclosure, the carrier body can also comprise at least one foot with an actuatable ram. The foot, in some variants of one or more embodiments can have a pressure cavity defined between the actuatable ram and a footing section of the carrier body, the pressure cavity fluidly connectable to a source of pressurizing fluid.

The present disclosure greatly reduces the size of the pressurizing equipment needed for high pressure processing. This is accomplished by creating small individual pressure chambers for each sample. Pressurizing fluid is communicated to each pressurizing chamber, and the applied pressure is transmitted though the elastic wall of the sample well. Because most fluids of interest are fairly incompressible, the amount of elasticity in many polymeric materials is sufficient to allow each filled tube to compress without resulting in its failure. In effect, 96, 48, or any number of samples can be processed in parallel, at the same time. By maintaining standard inter-well spacing, compatibility with downstream equipment will be maintained. The close fitting individual chambers allow the apparatus to use a minimum amount of pressurizing energy. This reduces the pressurization time and reduces the power and size of the high pressure pump needed for pressurization. In order to seal each tube sitting in its chamber, each tube is capped securely and each cap held in place. This can be accomplished by using a high clamping generated by a hydraulic lift, such as a foot, built into the carrier body.

Since high pressure is in each sample well, a net resulting force will be acting on the cap to separate it from its tube. For a standard microplate tube diameter of 0.25 inch, at a pressure of about 60,000 psi the lifting force will be approximately 3,000 pounds force per tube. To hold the cap in place, a clamping force of at least 3,000 pounds will be applied. When a 48 well format is used, the combined cap generated lifting force is about 141,000 pounds. A foot is utilized to provide the clamping force. When pressurized, the foot pushes the carrier body against the inside surface of the yoke. The foot would typically use the same pressure source as utilized to pressurize the pressure cells. By controlling the diameter of the actuating ram of the foot, a sufficient or greater clamping force than what is needed to counteract the force by pressure acting on the caps can be created. Thus, the cross sectional area of the foot is typically greater than the combined cross sectional area of the caps.

One aspect of the disclosure is directed to a pressurizable sample system comprising a microplate having a planar plate surface and at least one sample well. The at least one sample well has a flange positioned circumferentially around an outer surface of the at least one well and against the planar plate surface. The sample system further comprises a capping plate with a planar cap surface and at least one cap projecting from the planar cap surface. The at least one cap has a geometrical configuration in complementary correspondence with the configuration of the at least one sample well.

Embodiments of the sample system further may comprise a loading plate configured to contact and distribute an applied force across the capping plate to create a sealing pressure. The sample system further may comprise a carrier including a carrier body. The carrier body may have at least one pressurizing fluid port, at least one fluid channel fluidly connected to the at least one pressurizing fluid port, and at least one pressure cell fluidly connectable to the at least one pressurizing fluid port through the at least one channel. The at least one pressure cell may be defined by a cell cavity with an open end at a receiving surface of the carrier body. The at least one pressure cell may have a retaining flange positioned circumferentially around the open end of the cell cavity at the receiving surface of the carrier body. The at least one sample well may be configured to be received within the at least one pressure cell. The carrier further may include a casing having an inner cavity sized and configured to receive the carrier body.

Another aspect of the disclosure is directed to an apparatus for pressurizing a sample comprising a carrier body having at least one pressurizing fluid port, at least one fluid channel fluidly connected to the at least one pressurizing fluid port, and at least one pressure cell fluidly connectable to the at least one pressurizing fluid port through the at least one channel. The at least one pressure cell is defined by a cell cavity with an open end at a receiving surface of the carrier body. The at least one pressure cell has a retaining flange positioned circumferentially around the open end of the cell cavity at the receiving surface of the carrier body. The apparatus further comprises a casing having an inner cavity sized and configured to receive the carrier body.

Embodiments of the apparatus further may comprise a pressure generator fluidly connected to provide a pressurizing fluid into the cell cavity through the at least one pressurizing fluid port. The apparatus further may comprise a microplate having planar surface and at least one sample well at least partially defined by a sample well wall open at an end at the planar surface. The at least one sample well is sized to be at least partially contained within the at least one cell cavity. The at least one sample well may have a sealing flange circumferentially surrounding an outer perimeter of the sample well wall, at least a portion of the sealing flange contiguous with at least a portion of the planar surface of the microplate. The sealing flange may have a geometrical configuration corresponding with an inner geometrical configuration of the retaining flange. The apparatus further may comprise a capping plate with a planar cap surface and at least one cap projecting from the planar cap surface, the at least one cap having a geometrical configuration in complementary correspondence with an inner configuration of capping section of the at least one sample well. The apparatus further may comprise a loading plate configured to contact and distribute an applied pressure onto the capping plate. The carrier body further may comprise at least one foot with an actuatable ram. The foot has a pressure cavity defined between the actuatable ram and a footing section of the carrier body. The pressure cavity fluidly connects to a source of pressurizing fluid.

Yet a further aspect of the disclosure is directed to a method for pressurizing a sample. The method comprises: depositing a sample in a microplate having a planar plate surface and at least one sample well for receiving the sample, the at least one sample well having a flange positioned circumferentially around an outer surface of the at least one sample well and against the planar plate surface; and sealingly covering the at least one sample well with a capping plate with a planar cap surface and at least one cap projecting from the planar cap surface, the at least one cap having a geometrical configuration in complementary correspondence with the configuration of the at least one sample well.

Embodiments of the method further may comprise applying pressure on the capping plate with a loading plate configured to contact and distribute an applied pressure across the capping plate. The method further may comprises supporting the microplate with a carrier including a carrier body, the carrier body having at least one pressurizing fluid port, at least one fluid channel fluidly connected to the at least one pressurizing fluid port, and at least one pressure cell fluidly connectable to the at least one pressurizing fluid port through the at least one channel. The method further may comprise pressurizing the at least one pressure cell. The carrier further may include a casing having an inner cavity sized and configured to receive the carrier body.

BRIEF DESCRIPTION OF THE DRAWINGS

The accompanying drawings are not drawn to scale. In the drawings, each identical or nearly identical component that is illustrated in the various figures is represented by a like numeral. For purposes of clarity, not every component may be labeled in every drawing.

In the drawings:

FIG. 3 is another schematic illustration showing a different perspective view of a portion of the sample pressurizing system which may be implemented in accordance with one or more aspects of the disclosure;

FIG. 4 is a schematic illustration showing a microplate, capping plate, and load distribution plate which can be utilized in accordance with one or more embodiments of the disclosure;

DETAILED DESCRIPTION OF THE INVENTION

Figure 1:
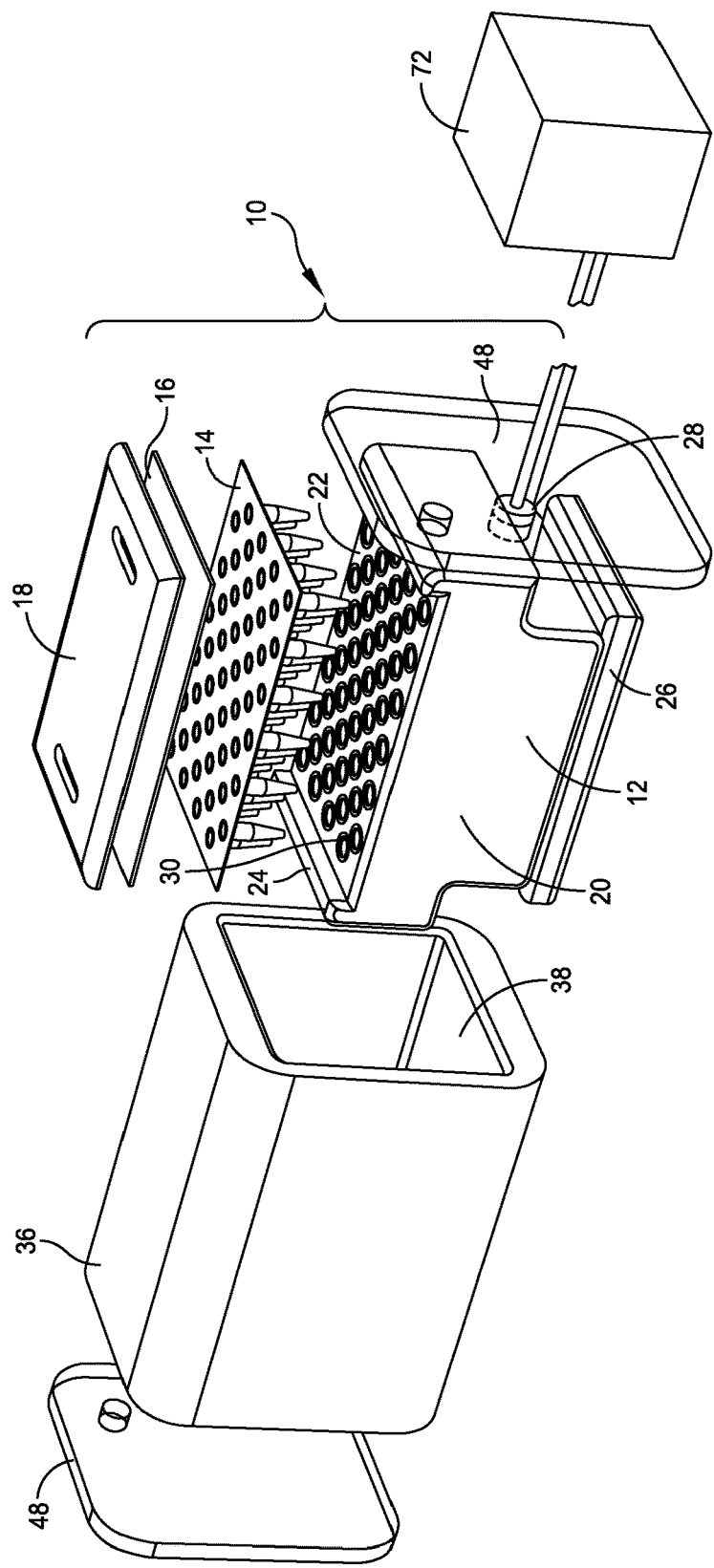
FIG. 1 is a schematic illustration showing components of a sample pressurizing system in accordance with one or more aspects of the disclosure.

Some aspects of the disclosure involve methods and systems for pressurizing a sample or sample mixture as well as to components thereof that facilitate exposing at least a portion of the sample to a pressurized condition. Pressurization of the sample mixture can involve exposing at least a portion of the sample to a pressure environment that differs from ambient. Pressurization can also involve, in some implementations of the disclosure, exposing at least a portion of the sample mixture to a plurality of pressurized environments or conditions.

One or more aspects of the disclosure can be directed to a sample pressurization system. The pressurizable sample system can comprise a microplate typically having a planar plate surface and at least one well which contains the sample to be pressurized. The sample pressurization system typically further comprises a carrier body having a receiving surface, at least one pressurizing fluid port, at least one fluid channel fluidly connected to the at least one pressurizing fluid port, and at least one pressure cell fluidly connected or connectable to the at least one pressurizing fluid port, typically through the at least one fluid channel.

The at least one pressure cell can be defined by a cell cavity that is formed within the carrier body. Further, the at least one pressure cell typically has an open end at the receiving surface of the carrier body. As exemplarily illustrated, the cell cavity can have a substantially circular cylindrical configuration with a frustoconically shaped section; however, other configurations can be utilized to implement or facilitate at least one aspect of the disclosure.

In accordance with still further aspects of the disclosure, the system for pressurizing the sample can also have a casing, such as a yoke, that retains the components of the sample pressurizing system in place during one or more pressure cycles or pressurization events. The casing typically has an inner or casing cavity sized and configured to receive the carrier body.

In one or more embodiments of the disclosure, the system can also comprise a pressure generator (not shown) fluidly connected to provide a pressurizing fluid into the cell cavity through the at least one pressurizing fluid port. Non-limiting examples of the sources of pressurizing fluid, e.g., a pressure generator, include commercially available instruments that can provide pressurized fluids at least 100 psi, and up to about 150,000 psi, such as the HUB 440 pressure generator from Pressure BioSciences, Inc., South Easton, Mass. Higher pressure, up to over 100,000 psi can be used as needed for the application or service.

The carrier body can also comprise at least one clamp that secures the carrier body to the casing during, for example, the one or more pressure cycles or pressurization events. As illustrated, the carrier body can have at least one foot with an actuatable ram that secures the carrier body within the casing. The clamp can be hydraulically or pneumatically actuated; for example, the foot can have a pressure cavity defined between the actuatable ram and a footing section of the carrier body. The pressure cavity can be fluidly connectable to a source of a pressurizing fluid through, for example, one or more actuating fluid ports.

The microplate can have a planar surface and at least one sample well that is typically at least partially defined by a sample well wall. The microplate is typically arranged with a 48 or 96 well array. However individual tubes may be used in the pressurizing cavities. The at least one sample well typically has an open end or aperture that is defined at the planar surface of the microplate. Advantageous configurations of the disclosure can involve a microplate with a plurality of orderly, uniformly spaced-apart sample wells, each of the sample wells having an open end at the planar surface. The at least one sample well is typically sized to be at least partially contained within the at least one cell cavity of the pressure cell. Further advantageous configurations of the sample system can involve microplates with a sample well that is shaped to geometrically complement or correspond with the shape of the cell cavity. For example, the sample well can have a circular cylindrical section with a frustoconical section and the cell cavity can have a corresponding circular cylindrical section and a corresponding frustoconical section. Optional configurations of the microplate involve embodiments without a skirt, which typically extends perpendicularly from and along the perimeter of the planar surface. In one or more embodiments pertinent to one or more aspects of the disclosure, the apparatus for pressurizing a sample can also comprise a microplate having planar surface and at least one sample well that is at least partially defined by a sample well wall which is open at one end, typically at the planar surface. The at least one sample well can be sized to be at least partially contained within the at least one cell cavity.

In one or more embodiments pertinent to one or more aspects of the disclosure, the at least one sample well can have a sealing flange circumferentially surrounding an outer perimeter seal of the sample well wall. As illustrated, the seal can be positioned at a portion of the circular cylindrical section and adjacent the open end of the sample well. Further, at least a portion of the sealing flange can be contiguous with at least a portion of the planar surface of the microplate. In one or more embodiments pertinent to one or more aspects of the disclosure, the sealing flange can have a geometrical configuration corresponding with an inner geometrical configuration of the retaining flange.

In one or more embodiments pertinent to one or more aspects of the disclosure, the apparatus for pressurizing a sample can also comprise a capping plate with a planar cap surface and at least one cap projecting from the planar cap surface. The at least one cap typically has a geometrical configuration in complementary correspondence with an inner configuration of capping section of the at least one sample well. A pierceable cap can be used so that later sample retrieval can be performed using an automated syringe needle.

If only some of the sample wells of a microplate is being used, e.g., without complete filling of each of the plurality of sample wells, blanks, water, or dummy tubes or structures can be used to displace the air that otherwise will be in the empty sample well.

In one or more embodiments pertinent to one or more aspects of the disclosure, the carrier body can also comprise at least one foot with an actuatable ram.

The pressurizable sample system can further comprise a loading plate configured to contact and distribute an applied pressure onto the capping plate.

Each of the at least one sample well of the microplate is typically positioned within a correspondingly sized and shaped pressure cell of the carrier body such that the microplate seal is engaged with the shoulder of the retaining flange. Correspondingly, a cap of the capping plate is engaged with the capping section of sample well. Each of the caps can thus have outer surfaces that engage with an inner surface of each sample well.

The at least one pressure cell can have a retaining member, such as a retaining flange or a lip retainer, which can be positioned, for example, circumferentially around the open end of the cell cavity and typically against or as part of the receiving surface of the carrier body. The retaining member typically has a configuration corresponding with the geometrical configuration of the seal. As exemplarily illustrated, the retaining member comprises a lip retainer or retaining flange with a shoulder circumferentially around the open end of the pressure cell. The shoulder is typically shaped and sized to correspond with a protrusion section of the seal that correspondingly surrounds the perimeter of the well. Such a configuration facilitates trapping the sealing flange material in a confined space such that the material cannot extrude during the application of high pressure. The elevated lip of the retaining flange can act as a force concentrator creating a zone of highly confined materials that inhibits leaking of the sample mixture, and in some case, the pressure cell.

One or more aspects of the disclosure can be directed to methods of pressurizing a sample. Any one or more of the methods of the disclosure can involve providing a microplate having at least one sample well, disposing a sample to be pressurized into the at least one sample well of the microplate, and exposing an external surface of the at least one sample well to a pressurizing fluid thereby pressurizing the sample therein. The method can further comprise disposing a capping plate having at least one cap configured to correspond with the at least one sample well, on the microplate.

The foot, in some variants of the disclosure can have a pressure cavity defined between the actuatable ram and a footing section of the carrier body, the pressure cavity can be pressurized by a pressurizing fluid to actuate the ram and displace the footing section against the yoke which secures the carrier body therein.

A sample mixture can be disposed in the at least one sample well of the microplate. The capping plate can then be disposed on the microplate such that a cap is engaged with the sample well to seal the sample mixture therein. The microplate/capping plate assembly can be disposed on the carrier body such that the at least one sample well is at least partially contained in a pressure cell with the sealing flange around the sample well in engagement with the retaining flange thereby sealing or closing the open end of the pressure cell. As illustrated, the microplate and capping plate assembly is sized and shaped to be engaged with the receiving surface of the carrier body. When utilized, a cover plate can then be disposed on the capping plate. Some arrangements of the disclosure can involve utilizing one or more features, such receiving surface shoulder, to facilitate alignment of the microplate, capping plate and cover plate.

The carrier body/microplate/cover plate assembly can be disposed within the casing cavity of the yoke. The clamping assembly can be actuated by introducing pressurized fluid through the actuating fluid port thereby displacing the carrier body and securing the loading plate against an inner surface of the yoke. The loading plate thus facilitates transfer of forces across the capping plate and the microplate to the receiving surface of the carrier body. In some configurations, the carrier body is sized to be at least partially contained within the yoke inner casing cavity and, upon actuation of the foot, secures within the yoke, the loading plate (if utilized), the capping plate, the microplate, to the receiving surface of the carrier body.

Referring to the drawings, and more particularly to FIG. 1, a sample pressurization system is generally indicated at 10. The sample pressurization 10 system includes a carrier 12, a microplate 14 adapted to be received within the carrier, a capping plate 16 disposed over the microplate, and a loading plate 18 disposed over the capping plate. The carrier 12 includes a carrier body 20 having a receiving surface 22 configured to receive the microplate 14, a receiving surface shoulder 24, a foot 26 upon which the carrier body rests, and a pressurized fluid port 28. The receiving surface 22 includes several pressure cells, each indicated at 30, formed therein that are in fluid communication with the pressurized fluid port 28.

As shown in FIG. 1, the sample pressurization system may be configured to be received within a yoke 36. The yoke may be configured with a casing cavity 38 to retain the components of the sample pressurizing system in place during one or more pressure cycles or pressurization events. The casing cavity of the yoke may be sized and configured to receive the carrier body. Open ends of the yoke are blocked by safety covers, each indicated at 48.

Figure 2:
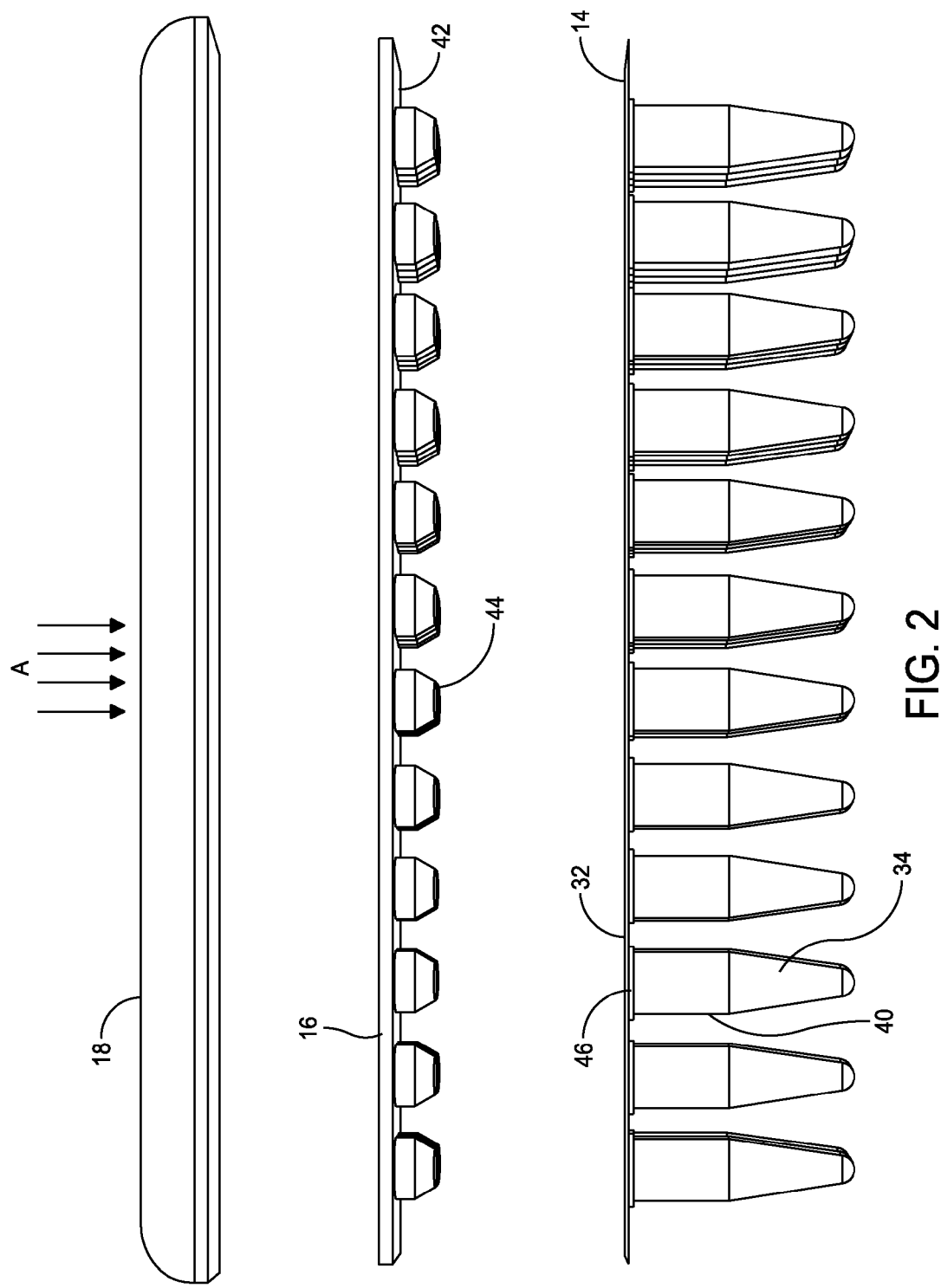
FIG. 2 is a schematic illustration showing a perspective view of a portion of the sample pressurizing system which may be utilized in accordance with one or more aspects of the disclosure may be practiced.

Referring to FIGS. 1 and 2, the microplate 14 has a planar plate surface 32 and several sample wells, each indicated at 34, formed in the planar plate surface, the sample wells being configured to contain samples to be pressurized. As shown, the microplate 14 has forty-eight sample wells 34, which are received in forty-eight corresponding pressure cells 30 formed in the receiving surface 22. It should be understood that the microplate 14 and the receiving surface 22 of the carrier body 20 may be configured to include any number of sample wells 34 and pressure cells 30, respectively.

Referring to FIG. 2, each sample well 34 of the microplate includes a sample well wall 40 that is cylindrical adjacent the planar plate surface 32 and tapered toward the bottom of the sample well. The capping plate 16 includes planar surface 42 having several downwardly projecting caps, each indicated at 44, that are arranged so that they are disposed over corresponding sample wells 34 of the microplate 14. The arrangement is such that the caps 44 sealingly engage corresponding sample wells 34 to ensure that samples are contained within the sample wells. In a certain embodiment, each cap 44 has a geometrical configuration in complementary correspondence with an inner configuration of capping section of the sample well 34. In another embodiment, a pierceable cap can be used so that later sample retrieval can be performed using an automated syringe needle. The arrangement is such that the loading plate 18 contacts and distributes an applied force across the capping plate 16 to create a sealing pressure.

The loading plate 18 is provided to provide downward pressure. Specifically, the loading plate 18 is configured to contact and distribute an applied pressure (as depicted by the arrows A in FIG. 2) onto the capping plate 16.

In certain embodiments, as described above, the microplate 14 embodies the planar surface 32 with the sample wells 34 partially defined by the sample well walls 40. The microplate 14 is typically arranged with a forty-eight or ninety-six well array. However, individual tubes may be used in the pressurizing cavities. Each sample well 34 has an open end or aperture that is defined at the planar surface 32 of the microplate 14. Each sample well 34 is sized to be at least partially contained within its respective cell cavity of the pressure cell 30. In other embodiments, each sample well 34 can have a sealing flange 46 circumferentially surrounding an outer perimeter seal of the sample well wall 40. As illustrated in FIG. 2, the seal 40 can be positioned at a portion of the circular cylindrical section of the sample well wall 40 and adjacent the open end of the sample well 34. Further, at least a portion of the sealing flange 46 can be contiguous with at least a portion of the planar surface 32 of the microplate 14. In a certain embodiment, the sealing flange 46 can have a geometrical configuration corresponding with an inner geometrical configuration of the retaining flange.

Advantageous configurations of the disclosure can involve a microplate with a plurality of orderly, uniformly spaced-apart sample wells, each of the sample wells having an open end at the planar surface. Further advantageous configurations of the sample system can involve microplates with a sample well that is shaped to geometrically complement or correspond with the shape of the cell cavity. For example, the sample well can have a circular cylindrical section with a frustoconical section and the cell cavity can have a corresponding circular cylindrical section and a corresponding frustoconical section. Optional configurations of the microplate involve embodiments without a skirt, which typically extends perpendicularly from and along the perimeter of the planar surface. In one or more embodiments pertinent to one or more aspects of the disclosure, the apparatus for pressurizing a sample can also comprise a microplate having planar surface and at least one sample well that is at least partially defined by a sample well wall which is open at one end, typically at the planar surface. The at least one sample well can be sized to be at least partially contained within the at least one cell cavity.

Referring to FIG. 3, the pressurized fluid port 28 (not shown in FIG. 3, but illustrated in FIGS. 1 and 4) is in fluid communication with a fluid channel 50. The fluid channel 50 provides fluid communication between the pressure cells 30 and the pressurized fluid port 28. As mentioned above, each pressure cell 30 may be defined by a cell cavity that is formed within the carrier body 20. Each pressure cell 30 may have an open end at the receiving surface 22 of the carrier body 20. As shown, the each cell cavity may have a substantially circular cylindrical configuration with a frustoconically shaped section to match the construction of the sample wells 34 of the microplate 14; however, other configurations can be utilized to implement or facilitate at least one aspect of the disclosure. The sample pressurization system 10 can also comprise a pressure generator 72 fluidly connected to provide a pressurizing fluid into the cell cavity through the pressurizing fluid port 28. Non-limiting examples of the sources of pressurizing fluid, e.g., a pressure generator, include commercially available instruments that can provide pressurized fluids at least 100 psi, and up to about 150,000 psi, such as the HUB 440 pressure generator from Pressure BioSciences, Inc., South Easton, Mass. Higher pressure, up to over 100,000 psi can be used as needed for the application or service.

Referring to FIGS. 3 and 4, the carrier body 20 can also comprise a clamp assembly that secures the carrier body to the yoke 36 during, for example, the one or more pressure cycles or pressurization events. As illustrated, the carrier body 20 has a foot 52 with an actuatable ram 54 that secures the carrier body within the yoke 36. The clamp can be hydraulically or pneumatically actuated; for example, the foot 52 can have a pressure cavity 56 defined between the actuatable ram 54 and a footing section 58 of the carrier body 20. The pressure cavity 56 can be fluidly connectable to a source of a pressurizing fluid through, for example, an actuating fluid port 60.

Referring to FIG. 4, the introduction of pressurized fluid into the pressure cavity 56 via the actuating fluid port 60 is shown. Specifically, the carrier body 20, the microplate 14, and the capping cover plate 16 assembly is disposed within the casing cavity 38 of the yoke 36. The clamping assembly is actuated by introducing pressurized fluid through the actuating fluid port 60 thereby displacing the carrier body 20 and securing the loading plate 18 against an inner surface of the yoke 36, as illustrated by arrows B in FIG. 4. The loading plate 18 thus facilitates transfer of forces across the capping plate 16 and the microplate 14 to the receiving surface 22 of the carrier body 20. In some configurations, the carrier body 20 is sized to be at least partially contained within the casing cavity 38 of the yoke 36 and, upon actuation of the foot 52, secures within the yoke, the loading plate 18 (if utilized), the capping plate 16, the microplate 14, to the receiving surface 22 of the carrier body 20.

Figure 6:
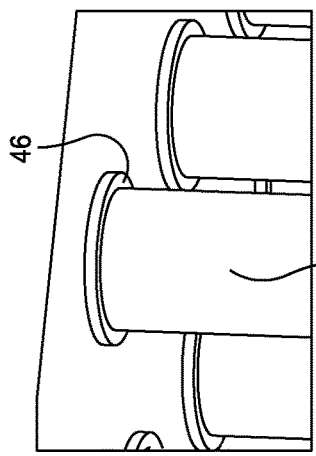
FIG. 6 is a schematic illustration showing a portion of a carrier body which can be utilized in accordance with one or more embodiments of the disclosure.
Figure 5:
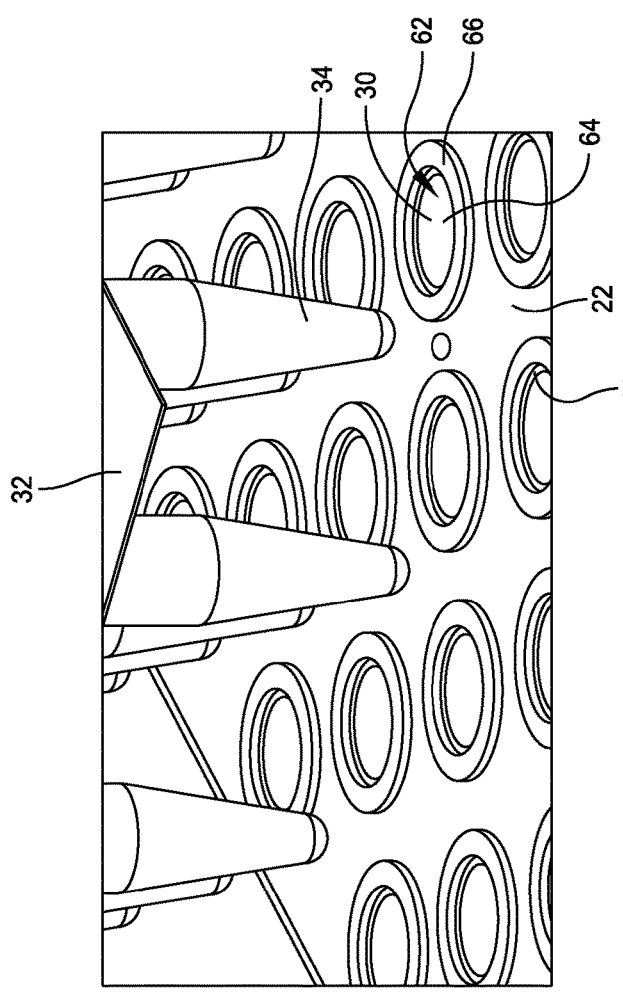
FIG. 5 is a schematic illustration showing a portion of a microplate which can be utilized in accordance with one or more embodiments of the disclosure.
Figure 7:
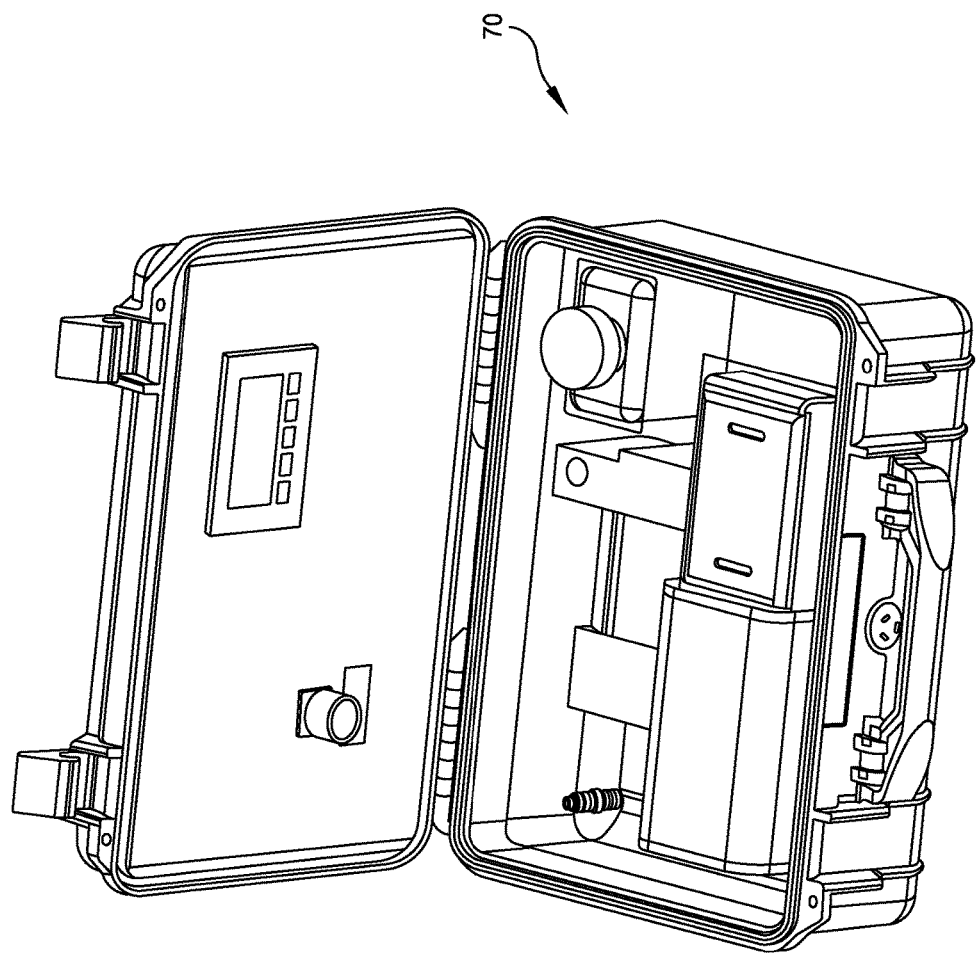
FIG. 7 is a schematic illustration of a compact sample pressurizing system which may be utilized in accordance with one or more aspects of the disclosure.

Referring to FIGS. 5 and 6, each pressure cell includes a cell cavity 62 having an open end 64 a retaining member, such as a retaining flange or a lip retainer 66, which can be positioned, for example, circumferentially around the open end of the cell cavity and typically against or as part of the receiving surface 22 of the carrier body 20. The retaining member 66 has a configuration corresponding with the geometrical configuration of the sealing flange 46. In one embodiment, the retaining member 66 includes a lip retainer or retaining flange with a shoulder 68 circumferentially around the open end 64 of the pressure cell 30. The shoulder 68 is shaped and sized to correspond with a protrusion section of the seal 46 that correspondingly surrounds the perimeter of the pressure well 30. Such a configuration facilitates trapping the material of the sealing flange 46 in a confined space such that the material cannot extrude during the application of high pressure. The elevated lip of the retaining flange 66 can act as a force concentrator creating a zone of highly confined materials that inhibits leaking of the sample mixture, and in some case, the pressure cell 30.

In one embodiment, the yoke 36 can also be constructed from high strength material. For example high strength precipitation strengthened stainless steel, such as 15-5 or 17-4 may be utilized as the material of construction of the yoke 36. If low overall weight is a consideration, as in a mobile application, a titanium or wire wound yoke design may be used. Thus, the present disclosure can be implemented as a portable, field deployable device contained in a portable housing, such as the field deployable device generally indicated at 70 in FIG. 6.

Pressurizing fluid from a pressure generator can be introduced into the at least one pressure cell through the fluid channel and the pressurizing fluid port. Because the pressure cell is sealed by the sealing flange and retaining flange assembly, the pressure of the pressure cell increases based on the pressure of the pressurizing fluid. Pressurizing fluid in the pressure cell then exerts an applied pressure on the surface of the sample well which typically at least partially deforms thereby transferring at least a portion of the applied pressure to the sample mixture contained within the sample well. Correspondingly, because the cap seals the sample mixture within the sample well, the sample mixture is exposed to the applied pressure.

Pressurization of the sample mixture can be implemented by utilizing a control system which can regulate the applied pressure from the source of pressurizing fluid and/or actuate valves that fluidly connect or isolate the pressure cell from the source.

Other implementations of the disclosure can involve utilizing assemblies without a foot as a clamping assembly. For example, a platen can be disposed to impinge against the capping plate thereby securing and sealing the contents of the sample well. The platen can be hand or motor actuated, e.g. with driven with one or more screws from the casing, to secure and seal the pressure cell and the sample well. Pressurizing fluid can then be introduced into the pressure cell to pressurize the sample mixture contained within the sample well.

One or more configurations of the disclosure can involve selectively pressurizing groups of pressure cells by selectively regulating the pressure or the introduction of the pressurizing fluid into such groups of pressure cells.

The apparatus, system and techniques of the present disclosure can be directed to pressure cycling, high pressure facilitated chemical synthesis, derivation, enzymatic reactions, such as protein digestion, protein deglycosylation, labeling, such as stable isotopic labeling for mass spectroscopic analysis, fluorescent labeling, and tagging with ultraviolet-absorbing chromophores for high pressure liquid chromatography (HPLC) and mass spectrometry as well as protein crystallization, pathogen inactivation, control of protein-protein and protein-DNA binding and immunochemical reactions. The various systems and techniques of the disclosure are, however, not limited as such and other applications relevant to pressure cycling sample preparation processes are contemplated. At least some aspects of the systems and techniques of the disclosure can be directed to modulating, facilitating, or effecting one or more reactions that can be at least partially pressure regulated by high pressure conditions in the sample mixture. One or more further aspects of the disclosure can involve pressurizing the sample or sample mixture by increasing or decreasing the applied pressure thereto, quenching or even initiating a chemical or enzymatic reaction step, moving the sample mixture into or from a subsystem or component to another component or subsystem, changing the pH of the sample mixture, and/or introducing one or more reagents that changes one or more characteristics of the sample mixture or initiates or terminates one or more reactions of one or more components of the sample mixture.

As used herein, a sample or a sample mixture can include one or more specimens, cultures, biological samples, and environmental samples from human and animal tissue as well as naturally occurring and synthetic materials. The sample mixture can include one or more organic compounds such as enzymes or enzyme substrates which are immobilized on surfaces wetted by the sample mixture. In some cases, however, the enzyme substrates can be suspended within the sample mixture.

The terms sample well and sample vessel are used to indicate a container for enclosing an amount or volume of the sample or sample mixture within a chamber, channel, annulus, or volume. The sample well is not limited to any one geometrical configuration or design and can be a container in which one or more actions or events, such as pressurization cycles or reactions, may occur. The volume of the sample well or the sample mixture to be pressurized can be less than about 1 mL, in some cases, less than about 0.1 mL, in other cases, less than about 0.01 mL, and in still other cases, less than about 0.001 mL. In still other configurations, the volume of the sample mixture to be pressurized can be 0.0001 mL to about 1 mL, in some cases, 0.001 mL to 0.1 mL, and in still other cases, 0.01 mL to 0.1 mL. Further configurations can involve pressurizing sample mixtures of 0.0001 mL (0.1 µL), 0.001 mL (1 µL), 0.005 mL (5 µL), or even 0.01 mL (10 µL).

Non-limiting examples of organic compounds that may be present in the sample mixture include natural and synthetic nucleic acids, nucleotides, oligonucleotides, α-amino acids, oligopeptides, peptidomimetics, depsi-peptides, peptides, saccharides, liposaccharides, and mixtures thereof. Organic compounds that can be present in the sample mixture also include radio-labeled compounds, and other compounds with detectable tags or signals. Non-limiting examples of the nucleotides that can be present as the one or more organic compounds include deoxynucleoside 5' triphosphates such as dATP, dCTP, dGTP, dTTP, and dUTP; dideoxynucleotides as well as nucleotides for resolving sequencing ambiguities such as c7dGTP, dITP, and c7dATP; 2'-deoxynucleoside-5'-O-(1-thiotriphosphates) such as dATPαS; 5-methyldeoxycytidine 5'-triphosphate; ribonucleoside 5'-triphosphates; 2'3'-ddNTPs; and 7-deaza 2'-dNTPs. Non-limiting examples of amino acids that can be present in the sample mixture include α-amino acids, Gly, Ala, Val, Leu, Ile, Ser, Thr, Asp, Asn, Lys, Glu, Gln, Arg, His, Phe, Cys, Trp, Tyr, Met, and Pro; and other natural or synthetic amino acids such as norleucine, ethylglycine, ornithine, methylbutenylmethylthreonine, phenylglycine, γ-carboxyglutaric acid, β-hydroxyproline, γ-hydroxyproline, δ-hydroxylysine, methylated amino acids, and ε-iodo, ε1-ε2-diiodo, ε-nitro-, ε-amino- and O-acetyl-tyrosine. Non-limiting examples of saccharides that can be present in the sample mixture include glucose, fructose, galactose, mannose, sucrose, and other substituted saccharides.

The sample mixture can also include ionized species such as inorganic or organic cationic or anionic species, non-limiting examples of which include lithium, sodium, potassium, magnesium, calcium, chromium, iron, manganese, zinc, cobalt, copper, and aluminum, fluoride, chloride, bromide, iodide, sulfate, phosphate, hydrogen phosphate, carbonate, and bicarbonate.

In some cases, the sample mixture can also include gases such as the noble gases, reactive gases such as HCl, HF, diatomic hydrogen, and diatomic halogen, and atmospheric gases such as carbon dioxide, carbon monoxide, and oxygen.

The sample mixture can include one or more solvents or mixture thereof such as methylene chloride, tetrahydrofuran, dimethyl formamide, ether, benzene, toluene, hexane, and ethyl acetate, ethyl alcohol, methyl alcohol, acetone, acetonitrile, trifluoroethanol, and 1.1.1.3.3.3-hexafluoro 2-propanol.

As used herein, a vector (or vehicle) is a nucleic acid molecule that transfers a DNA segment or segments from one cell to another. An expression vector is a recombinant DNA molecule containing a desired coding sequence and nucleic acid sequences necessary for the expression of the operably linked coding sequence in a particular host organism. Nucleic acid sequences for expression in procaryotes usually include a promoter, an optional operator, and a ribosome binding site. Eukaryotic cells are known to utilize promoters, enhancers, and termination and polyadenylation signals. Complementarity may be partial, wherein only some of the bases are matched according to the base pairing rules, or complete. The degree of complementarity between nucleic acid strands significantly affects the efficiency and strength of hybridization between nucleic acid strands. Complementarity therefore bears on the accuracy of amplification reactions, as well as detection methods dependent upon binding between nucleic acids. Hybridization is the pairing of complementary nucleic acids. Hybridization and the strength of hybridization, i.e., the strength of the association between the nucleic acids, is impacted by such factors such as the degree of complementary between the nucleic acids, stringency of the conditions involved, the Tm of the formed hybrid, and the G:C ratio within the nucleic acids. Tm is the melting temperature, or the temperature at which a population of double-stranded nucleic acid molecules becomes half dissociated into single strands. A simple estimate of the value of Tm may be calculated by $$Tm = 81.5 + 0.41 \quad (\% \ G+C),$$

when a nucleic acid is in aqueous solution at 1 M sodium chloride (NaCl), see e.g., Anderson and Young, Quantitative Filter Hybridization, in Nucleic Acid Hybridization (1985). Other references include more sophisticated calculations which take structural as well as sequence characteristics into account for the calculation of Tm. Stringency refers to the conditions of temperature, ionic strength, and the presence of other compounds such as organic solvents, under which nucleic acid hybridizations are conducted. Under high stringency conditions, nucleic acid base pairing will occur only between nucleic acid fragments that have a high frequency of complementary base sequences. Under weak or low stringency conditions, nucleic acids that are derived from organisms that are genetically diverse will occur, even though the frequency of complementary sequences is usually less.

As used herein, nucleic acid and nucleic acid substrate encompass DNA, RNA, and peptide nucleic acids (PNA), whether single stranded, double stranded, or a single strand with intermittent complementary segments, or combinations thereof. Chimeric oligonucleotides having stretches of both RNA and DNA residues on the same oligonucleotide are commercially available from, for example, oligos Etc., Inc., Wilsonville, Oreg. The present disclosure does not, in principle, limit the length of the nucleic acid; the nucleic acid may be genomic or a defined length, e.g. short oligonucleotides, or fragment thereof (including single bases). A nucleic acid may be obtained from any source and therefore may be naturally occurring; naturally occurring and purified; or produced synthetically, recombinantly, or by amplification. Nucleic acids include modified nucleic acids formed by an enzyme which removes a nucleotide from the nucleic acid substrate, or adds a chemical moiety, such as a terminal methyl group, or a linking group to bond the nucleic acid to another molecule. A nucleic acid may be immobilized on a polymer or composite bead, matrix, or other support surface. Nucleic acids may be amplified by any amplification method. Amplifiable nucleic acids typically include a sample template, which is typically a nucleic acid from the sample. A background template may or may not be present in the sample mixture, and is typically an inadvertent result of carryover, or from nucleic acid contaminants sought to be purified away from the sample such as those from organisms other than those to be detected, analyzed, characterized, or reproduced may be present as background in the sample mixture. Non-limiting examples of amplification methods include polymerase chain reaction (PCR), such as the method for increasing the concentration of a segment of a target sequence in a mixture of genomic DNA without cloning or purification disclosed by K. B. Mullis in U.S. Pat. Nos. 4,683,195 and 4,683,202, which is hereby incorporated by reference.

Enzymatic activity typically depends on the temperature, pressure, and solvent system (solvent and salts). Typically, preferred enzymatic activity can be in a temperature in a range of from about 10° C. to about 80° C., and can be in a range of from about 25° C. to about 37° C. Optimal enzymatic temperatures can be readily ascertained by consulting with literature from, for example, New England BioLabs, Ipswich, Mass. A substantially inactive enzyme typically exhibits less than about 20%, and generally less than 10%, of its activity at optimum enzymatic temperature (and atmospheric pressure) (100% activity). Ideally, an inhibited or substantially inactive enzyme is completely inactive (0% activity) but determination thereof may be limited by the sensitivity and uncertainty of a given activity assay. A reversibly inhibited enzyme exhibits no activity under restrictive or inhibitory conditions but can resume activity when exposed to permissive conditions or elimination of the restrictive conditions. Typically, a pause or transition period can occur after permissive conditions are imposed, but before enzymatic activity resumes. Permissive conditions include those conditions under which optimum enzymatic activity occurs, and also those conditions under which slower, but measurably useful activity occurs. A primer is typically an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method. A probe is typically an oligonucleotide, occurring naturally as in a purified restriction digest or produced synthetically, which is capable of hybridizing to another oligonucleotide of interest. Probes can be useful in the detection, identification, and isolation of particular gene sequences. A probe, the particular gene sequence, or both, can be labeled with one or more reporter molecule, so that the probe, the particular gene sequence, or both, can be detectable by, for example, ELISA, as well as enzyme-based histochemical assays, fluorescent, radioactive, and luminescent detection systems. A target sequence is the region of nucleic acid bounded by the primers used for detection and/or amplification, e.g., by the polymerase chain reaction. Thus, it is desirable to identify the target from among other sequences. A segment is a region of nucleic acid within the target sequence.

A PCR product or amplification product is the resultant mixture of compounds after two or more cycles of the steps of denaturation, annealing, and extension. These terms encompass the case where there has been amplification of one or more segments of one or more target sequences. Amplification reagents are those reagents needed for amplification exclusive of primers, a nucleic acid template, and an amplification enzyme. Amplification reagents include deoxyribonucleoside triphosphates and buffer. Typically, amplification reagents and other reaction components are placed in a reaction, e.g., sample, vessel, e.g., test tube, microwell, pressure deformable casing with optional outlets, etc.

Restriction endonucleases and restriction enzymes refer to enzymes (e.g., bacterial enzymes), each of which cuts double-stranded DNA at or near a specific nucleotide sequence.

DNA molecules are said to have 5' ends and 3' ends because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide can be referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being upstream or 5' of the downstream or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, an oligonucleotide having a nucleotide sequence encoding a gene refers to a DNA sequence comprising the coding region of a gene or in other words the DNA sequence which encodes a gene product. The coding region may be present in either a cDNA or genomic DNA form. Suitable control elements such as enhancers/promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc., or a combination of both endogenous and exogenous control elements.

Enzymes that synthesize or digest polymer substrates may dissociate from the substrate after each catalytic event, i.e., they may be non-processive (coextensive with distributive). They may remain bound to the polymer until many cycles of reaction are completed, i.e., they may be processive.

Further features of the disclosure can involve addition of components to the sample mixture.

Some configurations of the systems of the present disclosure may be utilized in techniques or applications wherein at least one step of a reaction thereof is pressure-sensitive. Non-limiting examples of such techniques or applications include enzymatic, non-enzymatic, chemical, physical, kinetic, and thermodynamic reactions or wherein pressure-sensitive interactions which can involve covalent bond breaking and bond formation, non-covalent, ionic, hydrogen bonds, and van der Waals forces; hydrophobic or hydrophilic interactions; and structural modifications such as secondary, tertiary, and quaternary, i.e., folding, and formation of helices and sheets. Various aspects of the disclosure can involve modification or altering at least one characteristic, such as a rate of a reversibly pressure-sensitive reaction step. For example, one or more pressure-sensitive reactions that can be altered can include those that have a rate that can be decreased, stopped, increased, or started. Particular embodiments can thus involve changing from a characteristic inhibitory pressure to a characteristic permissive pressure. In accordance with still further aspects of the disclosure, any of the systems and techniques described herein can further involve utilizing one or more incubation periods to promote or create one or more desirable conditions or to effect or promote one or more of conversion, transformation, and characterization of one or more components. The one or more incubation periods or events can involve maintaining any one of a pressurized, depressurized, cooling, and heating activities. The duration of any one or more of such activities can vary from about one second to about thirty minutes. In some cases, any of the one or more incubation periods can progress at changing conditions and is not limited to being performed at a steady or constant state. For example, any of the one or more periods can be performed while the temperature of the sample liquid is increasing or decreasing, preferably at a predetermined rate.

In accordance with further embodiments of the disclosure, at least a portion of a surface of the sample cell wall can comprise one or more pendent moieties that can bond to one or more target species or ligands, in the sample mixture. Other embodiments of the disclosure can involve utilizing beads or components that have at least one surface-active moiety which can bind to at least one target species.

A pressure cycle or pressurization event can be the summation of exposing the sample mixture to more than one pressure for a period of time at each pressure, e.g., raising the pressure and lowering the pressure, e.g., up from a first pressure to a second pressure and then down from the second pressure to a third pressure. Further, a second pressure cycle or pressurization event can be carried out, e.g., from the third pressure to a fourth pressure to a fifth pressure, and so forth. This process can be repeated. For example, a pressure cycle can consist of exposing the sample mixture, e.g., the mixture being exposed to pressure cycles, which typically has one or more components of interest, to a first pressure for a first period of time; exposing the sample mixture to a second pressure for a second period of time; and then exposing the sample mixture to a third pressure for a third period of time. There is no limit to the number of pressurization events that the sample can be exposed to, and the period of time spent at each pressurization event can vary and need not have the same duration.

The various apparatus of the present disclosure can be utilized to modify and/or control activity or characteristics of the sample mixture or components thereof. For example, the various systems and techniques of the present disclosure can facilitate nucleic acid sequencing, nucleic acid synthesis, protein sequencing, enzymatic chiral synthesis, and enantiomeric purification of racemic mixtures. Non-enzymatic reactions can also be controlled by utilizing one or more aspects directed to the various systems and techniques of the present disclosure. Desired effects of pressure upon the components of the sample mixture may include, for example, protein unfolding, protein folding, reversible inhibition of enzymatic activity, activation of enzymatic activity, and shifts in the reaction rate and the thermodynamic equilibrium of non-enzymatic reactions. Pressure-induced inhibition includes inhibiting a single enzymatic reaction step, several sequential enzymatic reaction steps, or the complete enzymatic event. Furthermore, an inhibitory pressure can synchronize the activity of individual reactant molecules, e.g., enzyme, cofactor, or first or second substrate. When the pressure is changed to a permissive pressure, multiple enzyme molecules begin to act at more or less the same time, resulting in more uniform, accurate, and reproducible control of enzymatic activity. A molar excess of enzyme to substrate, if any, usually increases synchronous behavior. Enzymatic reaction steps include the mechanistic steps involved in the reaction between an enzyme (E) and a substrate (S) to form a product (P). Depending on the complete enzymatic event, these steps include conformational change of E, S, P, and combinations thereof; association or dissociation of E-S and E-P; interaction between cofactor and either S or E; interaction among S, E, and a cofactor; solvent interaction with E, S, or a cofactor; proton exchange between E and a component of the sample mixture, such as S, a solvent, or a cofactor; and a catalytic interaction between E and S. Depending on the enzymatic event, there can be more than one substrate (S, S', S" and so on), more than one product (P, P', P" and so on), and more than one cofactor. Furthermore, some embodiments use more than one solvent or solute, e.g., salt or metal ion, and temperature in conjunction with pressure to provide inhibitory or permissive conditions which control an enzymatic reaction step.

Similarly, changing the pressure of the sample mixture to a pressure which can permit an enzymatic reaction step to occur can result in the occurrence of a subsequent enzymatic reaction step, a series of enzymatic reaction steps, or one or more complete enzymatic events. The various systems and techniques of the present disclosure can be utilized to control enzymatic activity by programming the desired series of single enzymatic events. For example, hyperbaric treatment that causes many biological macromolecules such as proteins, enzymes, antibodies, and polynucleotides to unfold or denature, which naturally function at pressures of 1 atmosphere. Such unfolding can effect inhibition of enzyme activity. Further, some enzymes or proteins, in particular those which naturally function at high pressures, e.g., in deep sea vent organisms, can be inhibited at lower pressures conditions.

The concentrations, buffers, solvents, enzymes, substrates, and other additives or facilitating molecules utilized in the various approaches of the disclosure may be utilized. Where advantageous, higher than usual concentrations of enzyme can be present to achieve more uniform and reproducible results. Those in the art are familiar with commercial sources for nucleic acids, markers, linkers, primers, buffers, amino acids, protecting groups, solvents, enzymes, and other related reagents, e.g., Aldrich, Milwaukee, Wis.; Pharmacia Biotech, Piscataway, N.J.; Promega Corp., Madison, Wis.; Sigma-Aldrich, St. Louis, Mo.; and Stratagene, La Jolla, Calif.

Applied hydrostatic pressure by, for example, pressure cycling, can be used to alter mutual solubility or miscibility of solvents in mixtures, e.g., azeotropic mixtures, solutions, suspensions, or multi-phase mixtures; to control the arrangement of molecules in micelles, emulsions, gels or colloids; and/or to control the dissolution of one or more components of the multi-phase mixture in another component or solvent. The various systems and techniques of the present disclosure can thus utilize changes in pressure to effect changes in mutual solubility of the components and depressurization of the system and, in some cases, can cause the mixture to break into multiple phases, thereby separating molecules into separate phases based upon the physiochemical properties.

Further, the various systems and techniques of the present disclosure can involve hydrostatic pressure to facilitate preparation of colloids or nanomaterials by dissolving components in one solvent, mixing the first solvent with another solvent, thereby leading to the formation of immiscible multi-phase mixtures when the first solvent is under atmospheric pressure. Pressure can also be used to control the size of micelles in a multi-phase system or emulsion to alter its physical property or stability.

A variety of liquids can be used in the liquid phases of the various systems and techniques of the present disclosure. For example, solvents, detergents, buffers, chaotropic agents, e.g., chaotropic salts, and mixtures thereof can be used.

A variety of solvents can be employed in accordance with one or more aspects of the present disclosure. For example, the one or more solvents can be aqueous, organic, or lipid. The solvent system can thus form multi-phase mixtures, e.g., of poorly miscible reagents. For example, the solvent system can be biphasic or triphasic.

In some embodiments, at least two solvent phases, e.g., liquid phases, can be used, with at least two solvent phases that are not mutually miscible at one of the pressures of the pressure cycle, e.g., the solvent phases are not mutually miscible at the first pressure. Upon pressure cycling, the two solvent phases can become at least partially mutually miscible and, in some cases, partially mutually soluble, at the other pressure, e.g., at the second pressure, such as where the second pressure is greater than the first pressure. Upon return to the first pressure, or transition to a third pressure, typically at lower than the second pressure, the partial mutual miscibility is removed and the solvent phases typically separate. In some embodiments of the present disclosure, depending on the choice of solvent phases used, the solvent phases can become fully miscible (and in some cases, fully soluble) at the second pressure.

Protic or aprotic solvents may also be utilized. Examples of protic solvents include water, methanol, ethanol, formic acid, hydrogen fluoride, and ammonia. Examples of aprotic solvents include dimethyl sulfoxide, dimethylformamide, hexamethylphosphorotriamide, and mixtures thereof. Non-limiting examples of solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diglyme (diethylene glycol dimethyl ether), 1,2-dimethoxy-ethane (glyme, DME), dimethylether, dimethyl-formamide (DMF), dimethyl sulfoxide (DMSO), dioxane, ethanol, ethyl acetate, ethylene glycol, glycerin, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, water, heavy water ($D_2O$), o-xylene, m-xylene, p-xylene, and mixtures thereof. Further non-limiting examples of solvents that may be utilized in various aspects of the present disclosure include chloroform, tetrachloroethylene, methanol, isopropanol, ethanol, water, aliphatic hydrocarbons, e.g., hexane and heptane, acetonitrile, formic acid, trifluoroacetic acid, glycerol, a lipid, e.g., triglyceride, phospholipid, sphingolipid, glycolipidsoil, e.g., from the sample itself, e.g., from a biological membrane, e.g., lipid membrane; lipid bilayer, or aqueous solution, e.g., a liquid component(s) that originates from the sample itself, e.g., from a biological membrane or cytoplasm, a fluorocarbon, other halocarbon, dimethyl sulfoxide (DMSO), fluorinated alcohols, e.g., amphiphilic fluorinated alcohols, e.g., 1,1,1,3,3,3-hexafluoro-2-propanol (HFIP), 2,2,2-trifluoroethanol (TFE), 2-fluoroethanol, 2,2,3,3-tetrafluoropropan-1-ol, 1,3-difluoropropan-2-ol, perfluorooctanol, other alcohols, and mixtures thereof. In some embodiments, the sample or sample mixture, e.g., the source of components, provides, e.g., functions as, a solvent. In some cases, this solvent from the sample constitutes one of the liquid phases of the extraction system. For example, in the extraction of a membrane protein, under appropriate conditions, the lipid bilayer acts as a solvent and as a liquid phase in the extraction method, e.g., the membrane protein is dissolved in the lipid bilayer.

As noted, mixtures of any of the solvents described herein can also be used.

The concentrations of the solvent can be tailored to particular requirements. Non-limiting examples of concentrations of solvents that may be utilized in the various aspects of the present disclosure include: about 0.2M HFIP; about 0.05M HFIP; about 0.38M to about 0.57M HFIP; about 60% HFIP; about 75% HFIP; about 95% HFIP; about 100% HFIP; about 1% to about 5% formic acid. The solvents can be made up in various other solvents, e.g., acetonitrile, or buffers, e.g., phosphate buffered solution (PBS). The solvents can be used by themselves to constitute a phase in the methods described herein. Alternatively, a solvent, e.g., a solvent listed herein, can be a solvent that, along with another component, e.g., a liquid, e.g., another solvent, make up one solvent phase. For example, 50% acetonitrile with 0.1% formic acid can make up on solvent phase, as illustrated in the examples herein.

A single solvent phase can include a combination of solvents. For example, a solvent phase can be chloroform:methanol:water in a 2:5:2 or 4:4:1 (w:w:w) ratio; or methanol:chloroform in a 1:1 (w:w) ratio. As another example, 50% acetonitrile with 0.1% formic acid can be used as a solvent phase.

The solvents can include an azeotrope, or an azeotrope can form when solvent phases are exposed to one or more pressurization events in accordance with some aspects of the present disclosure. Thus, where azeotropic mixtures that can act as different solvents by exhibiting altered solubility and ability to dissolve other compounds, such azeotropic solvent systems can be implemented to effect one or more features of the present disclosure. Hydrostatic pressure can alter the properties of azeotropic solvent mixtures as it alters properties of individual solvents. Non-limiting examples of azeotropes that can be implemented in the present disclosure include 95.5% ethanol and 4.5% water (w:w); 20.2% hydrogen chloride and 79.8% water (w:w); 1.2% water and 98.8% diethyl ether (w:w); 20% acetone and 80% chloroform (w:w); 30% acetone, 47% chloroform, and 23% methanol (w:w:w).

In some embodiments, one or more solvents can be added to the sample mixture to facilitate the formation of two or more liquid phases. For example, the addition of a solvent, e.g., an amphiphile such as HFIP, to a sample that contains one or more hydrophilic and/or polar components and one or more lipids can result in the formation of stable mixtures with the one or more hydrophilic and/or polar components and the one or more lipids, e.g., upon exposure to an increased pressure level. When pressure is decreased, the one or more hydrophilic and/or polar phases, e.g., HFIP, and one or more lipids separate into two or more liquid phases, e.g., thereby leading to the separation of components into the hydrophilic and/or polar or lipid phases, e.g., leading to the separation of a component of interest. In some embodiments of the disclosure, one solvent can be added to a sample mixture, which can effect the formation of two or more liquid phases, e.g., the sample provides a solvent(s), e.g., liquid phase. The addition of a solvent, e.g., an amphiphile such as HFIP, to a sample mixture that contains water and lipids can result in the formation of stable mixtures with water and the lipids, e.g., upon exposure to an increased pressure level. When pressure is decreased, the water, e.g., and HFIP, and lipids separate into two or more liquid phases, e.g., thereby leading to the separation of components into the water and lipid phases, e.g., leading to the separation of a component of interest.

In some embodiments, an organic solvent, e.g., a volatile organic solvent, e.g., HFIP, may need to be removed. For example, the removal of a volatile organic solvent can be accomplished by evaporation. In some embodiments, the removal of the volatile organic solvent can be accomplished by precipitation of the component(s) of interest. Subsequently, remaining solvent can be separated from the resulting pellet. Precipitation can be accomplished from a solvent, e.g., HFIP, by the addition of the appropriate component, e.g., an aqueous solution. Precipitation efficiency can be modified by sample concentration, temperature, pH, time, pressure, and the addition of other solutes, e.g., salts, chaotropic agents, detergents, or other components.

A variety of buffers can be used with the various systems and techniques described herein. For example, PBS can be used in a solvent phase of the methods. A wide variety of buffers can be used to maintain a desired pH of an extraction solvent and to maintain the solubility of desired components in a particular solvent and compatibility with a subsequent analytical method. Examples of such buffers include HEPES, TRIS, MES, ammonium bicarbonate, ammonium acetate, formic acid, trifluoroacetic acid, acetic acid, etc.

Various concentrations of salts can be used to control osmotic pressure in accordance with one or more aspects of the present disclosure. For example, a 0.9% sodium chloride can be used in the preparation or conditioning of components from mammalian cells. Osmotic pressure that can act synergistically with hydrostatic pressure can be utilized during pressure cycling in accordance with the present disclosure. For example, hypotonic concentrations of salts in the extraction solution can result in cell swelling and can act synergistically with the pressure cycling treatment to disrupt cellular plasma membranes. Conversely, hypertonic salt concentrations can be used to protect cells from disruption at certain pressure cycling conditions. For mammalian cells, NaCl concentrations below about 0.9% are typically hypotonic, and concentrations above about 0.9% are typically considered hypertonic.

One or more detergents or chaotropic agents, e.g., chaotropic salt, can be added to a solvent phase in accordance with one or more aspects of the present disclosure. In some embodiments, the amount of detergent used can be less than the amount used for known partitioning techniques, such as techniques based on mechanical shaking. In some embodiments, when a detergent is used in the methods described herein, no foaming is formed during the extraction. Non-limiting examples of detergents that can be used in one or more embodiments of the present disclosure include anionic detergents, e.g., SDS, Cholate, Deoxycholate; cationic detergents, e.g., C16TAB; amphoteric detergents, e.g., LysoPC, CHAPS, Zwittergent 3-14; and non-ionic detergents, e.g., Octylglucoside, Digitonin, C12E8, Lubrol, Triton X-100, Nonidet P-40, Tween 80. Several amphiphylic organic solvents, such as fluorinated alcohols, such as HFIP, TFE, perfluorooctanol, etc., can be regarded as possessing detergent functionality. Such solvents can be used alone or in combination, as an additive to other solvents and buffer systems, e.g., solvent and buffer systems described herein. The concentration of detergent used can be, for example, from about 0.001% to about 10%, e.g., about 0.1% to about 2%, e.g., about 0.5% to about 4%, e.g., about 1% to about 2%. However, in some embodiments of the present disclosure, the sample mixture can be free or substantially free of a detergent.

As noted, one or more chaotropic agents can also be used. Examples of such agents include urea, guanidinium chloride, guanidinium isothiocyanate, and guanidine hydrochloride. The concentration used can be about 0.1M to about 8M. Examples of chaotropic agents include those described, e.g., in U.S. Pat. No. 7,064,192 and U.S. Patent Application Publication Nos. 2006/0188970, 2004/0038333, 2003/0083475, and 2002/0137157.

Additional reagents may also be utilized. For example, one or more enzyme inhibitors, e.g., one or more of protease inhibitors such inhibitors of serine, cysteine, and aspartic proteases, and aminopeptidases, 4-(2-aminoethyl)benzenesulfonyl fluoride (AEBSF), pepstatinA, E-64, bestatin, leupeptin, and aprotinin, DNAse inhibitors, aurintricarboxylic acid, RNAse inhibitors, diethylpyrocarbonate (DEPC), Cesium Trifluoroacetate (CsTFA), recombinant placenta RNAse inhibitor, SUPERASE•INT™, ANTI-RNase or RNASECURE™ (Ambion), SCRIPTGUARD™ (Epicentre Biotechnologies), DEPC, metal chelating agents (e.g., DTPA, EDTA, EGTA, NTA, desferal) can be utilized to stabilize a component of interest.

Mineral oil can also be utilized to improve band sharpness and intensity. Other agents that effect improved phase separation which allows for efficient partitioning of endogenous lipids in a sample into the oil layer during centrifugation may be utilized.

High concentrations of salts that affect the extent of precipitation of certain proteins may also be utilized to effect interference with or to promote protein precipitation. Typically, endogenous sample-derived salts are insufficient to cause any significant effects upon precipitation. In many instances, exogenous salts can be added to improve total protein precipitation. In addition, optimized salt concentrations can be used to selectively precipitate desired proteins and retain undesired proteins in the supernatant and vice versa. For example, such an approach can be used to deplete a complex sample of highly abundant protein species, e.g., serum albumin, immunoglobulins, etc., and enrich for the low abundance proteins of biological significance.

The systems and techniques described herein can be performed alone or in combination with one or more additional steps/methods to facilitate, for example, isolation of a component of interest. The one or more additional steps can be performed before or after one or more pressurization events. For example, centrifugation, e.g., gradient centrifugation or ultracentrifugation or centrifugation in the same vessel, precipitation or precipitation of one or more sample components, immunoprecipitation to remove a contaminant, permeablization of a cell, with or without a detergent, using hypotonic buffer conditions to disrupt the plasma membrane or other membranes surrounding organelles, enrichment for a particular tissue, cell or organism type, membrane fraction, etc.; fractionation of sample constituents according to their localization in the cell or tissue or according to their physiochemical properties, e.g., electrostatic charge, hydrophobicity, solubility in a particular solvent, molecular conformation or binding affinity, etc., can be performed along with an extraction method provided herein to improve the isolation or purification of a component of interest.

The systems and techniques of the present disclosure can be used to extract or separate one or more components of interest from the sample mixture. Non-limiting examples of sources upon which the present disclosure may be utilized include biological and synthetic, e.g., man-made, sources. Examples of sources of biological origin include mammalian, e.g., human or domesticated animal, fungal, bacterial, viral, and plant sources. Examples of such sources include a cell, an organelle, e.g., mitochondrion, nucleus, Golgi apparatus, chloroplast, endoplasmic reticulum, vacuole, acrosome, centriole, cilium, glyoxysome, hydrogenosome, lysosome, melanosome, mitosome, myofibril, nucleolus, parenthesome, peroxisome, ribosome, microsome, vesicle, a membrane, e.g., a lipid membrane, e.g., a lipid bilayer, a biological sample (tissue sample (adipose tissue, liver, kidney, skin, pancreas, stomach, intestine, colon, breast, ovary, uterine, prostate, bone, tendon, cartilage, hair, nail, tooth, heart, brain, lung, skin, nerves, biopsy, etc.), blood, urine, milk, semen, saliva, mucus, other bodily fluids and solids)), collection of cells, e.g., blood, semen, mucus, saliva, tissue biopsy. Examples of other sources include butter, cream, a pharmaceutical or cosmetic formulation (ointment, lotion, cream, shampoo, conditioner, nanoparticle drug formulation, etc.), a pharmaceutical formulation in a tablet, capsule or gelcap form, a multi-phase composition such as emulsion or suspension of solid particles (ink, paint (e.g., latex paint), lacquer, lubricant, fuel, ingredients for chemical synthesis, etc.)), suspension of liposomes, membrane vesicles, liquid propellants, fuels, elastomers, polymers, ink formulations; emulsions of oil in water and other solvents such as industrial lubricants, soil, e.g., suspensions of soil samples, minerals, and so forth.

Examples of components, e.g., molecular entities, of the sample mixture include a protein, e.g., membrane bound protein, transmembrane protein, type I or type II membrane protein, receptor, enzyme, a lipoprotein, a glycoprotein, a polysaccharide, e.g., heparin or heparin-derived polysaccharide, starch, insulin, etc., a proteoglycan, e.g., collagen, chitin, murein, etc., a polyphenol, e.g., a tannin, a phenylpropanoid, e.g., a lignin, a flavonoid, a vitamin, a toxin, a pollutant, a lipid, e.g., phospholipids, e.g., phosphatidylcholine (PtdCho), phosphatidylethanolamine (PtdEtn), phosphatidylinositol (PtdIns), phosphatidylserine (PtdSer)), glycolipids, steroids, e.g., estrogen, progesterone, androgen, testosterone, ecdysteroids such as ecdysterone, corticosteroids such as glucocorticoids and mineralocorticoids, anabolic steroids, cholesterol, phytosterols, brassinosteroids, ergosterols, a membrane (cell membrane, organelle membrane, lipid bilayer), a nucleic acid (DNA (nuclear DNA, mitochondrial DNA), RNA (mRNA, tRNA, rRNA, mtRNA, microRNA)), a virus, e.g., HIV, HPV, hepatitis A, B, C, D, E, F, or G, cytomegalovirus, Epstein-Barr virus, yellow fever, a bacterium, e.g., Gram positive or Gram negative bacteria, mutualist bacteria, pathogenic bacteria, a component present in a bacterial cell or in a cell of other microorganism or other cell type, e.g., a protein recombinantly produced by the bacterium, yeast or a mammalian cell, recombinant proteins contained within the inclusion bodies, bacterial DNA or RNA, an antigen, e.g., from a bacterium, fungal or mammalian cell or from a virus, a virus, e.g., for vaccine production, a pharmaceutical agent such as a small molecule, a metabolite, e.g., a small molecule metabolite, a pesticide, e.g., bactericide, fungicide, herbicide, insecticide, e.g., ovicide, larvicide or adulticide, miticide, molluscicide, nematicide, rodenticide, virucide, a drug, e.g., a pharmaceutical drug, a drug metabolite, a dye, a food constituent, a nanoparticle formulation, a lipid raft, an amyloid plaque, microtubule, cytosol, oils, terpenes, and other lipophilic compounds, e.g., from plant material, various compounds, e.g. alkaloids, flavonoids, isoflavons, proanthocyanidins, anthocyanins from plants, e.g., medicinal plants, food flavor constituents, e.g., capsaicin, from food preparations, lipid-soluble vitamins, e.g., tocopherols, carotenoids, lycopene, etc, from plant oils or animal fat, topical drug formulation constituents, e.g., from skin and underlying tissues, a particular cell type, polymer, elastomer, lubricant, pigment, plasticizer, and so forth. For example, extraction of membrane proteins from lipid-rich adipose tissue or extraction of enzymes such as cytochromes P450 from liver microsomal fraction is greatly simplified and higher yields of desired proteins are obtained.

Examples of cell types include blastomere, egg, embryonic stem cell, epithelial cell, erythrocyte, fibroblast, hepatocyte, leukocyte, myoblast, myotube, neuron, oocyte, osteoblast, osteoclast, sperm, T-cell, zygote (animal or plant), aleurone, collenchyma, endodermis, endosperm, epidermis, mesophylll, meristematic cells, palisade, parenchyma, phloem sieve tube, pollen generative, pollen vegetative, sclerenchyma, tracheids, xylem vessel. Also included are various types of keratinizing epithelial cells, wet stratified barrier epithelial cells, exocrine secretory epithelial cells, hormone secreting cells, gut, exocrine glands and urogenital tract cell, metabolism and storage cells, barrier function cells (lung, gut, exocrine glands and urogenital tract), epithelial cells lining closed internal body cavities, ciliated cells with propulsive function, extracellular matrix secretion cells, contractile cells, blood and immune system cells, sensory transducer cells, autonomic neuron cells, sense organ and peripheral neuron supporting cells, central nervous system neurons and glial cells, lens cells, pigment cells, germ cells, nurse cells.

Reactants can be used in various configurations of the systems and techniques of the present disclosure. The one or more sample wells can have one or more subchambers (not shown) that contains one or more reagents. The one or more reagents can then be released and introduced into the sample mixture upon rupture of containment structures that confine the one or more reagents. Rupture and release of the one or more reagents can be initiated upon application of pressure by, for example, the pressurizing fluid.

Further configurations in accordance with one or more aspects of the present disclosure include restraint systems that allow separation or collation of components of the sample mixture by size, charge, polarity, chirality, or combinations thereof. Non-limiting examples of restraint systems comprise semi-permeable material such as a membrane or matrix. The semi-permeable material may occupy a complete cross-section of the sample well in the manner of a filter or net (not shown). The restraint, such as a semi-permeable barrier, can divide the sample well into two segments. More than one semi-permeable barrier can be utilized to divide the contained volume of the sample well into more than two segments.

Further configurations in accordance with one or more aspects of the disclosure can involve the use of immobilized substrates within the sample well. Such immobilization systems can comprise at least one permeable, or semi-permeable, membrane, typically having pores which can allow one or more components of interest, e.g., enzyme and products or small molecules to pass through; and another membrane has pores which allow only products or small molecules to pass through. The semi-permeable material may be configured as a rigid or flexible pouch, bag, or envelope attached to a wall of the sample well. For example, the one or more sample wells can include a porous plastic or glass plug with an immobilized reactant or reagent (either enzyme or substrate); or a membrane support on an interior surface of the sample well which supports a porous membrane containing an immobilized reactant. Additional examples include a rigid, hollow porous frit containing an immobilized reagent, wherein the frit is attached to an interior surface of the sample well. In some embodiments, the restraint can be moved to provide a semi-permeable barrier and then temporarily removed during a programmed series of cycles to allow free flow of all components out of the sample well. Preferably, the separation material is generally chemically inert with respect to the sample mixture components and structurally resistant to fluid pressures as high as the inhibitory pressure(s) in a particular application. Size-discriminating membranes or films include DIAFLO™ ultrafilter membranes, available from Amicon, Beverly, Mass., which are commercially available in molecular weight cut-offs ranging from 0.5 to 300 kD. Membranes can be utilized to separate enzymes from free nucleotides or amino acids; and immobilized substrates from free enzymes and free nucleotides or amino acids in solution. A separation material such as a membrane or matrix may be impregnated, coated, or otherwise functionalized with a substance or covalently bonded ligand which can interact with a component of the sample mixture. Materials having asymmetric surface properties or asymmetric pore channel hydrophobicity, hydrophilicity, and/or size, may be used. The semi-permeable material can also include analogs of column chromatography, whereby chiral separations are achieved using packed materials through which at least one sample mixture component is eluted.

Depending on the reaction involved and the restrictive properties of the restraint selected, the fluid can include a nucleotide, an amino acid, an enzyme, an unbound enzymatic substrate, a cofactor, and various solvents or salts. Similarly, the components of the sample mixture can also include solvents, salts, enzyme, a free substrate, or an immobilized reagent. Immobilized reagents can include organic compounds attached to a non-liquid support. Examples of a support include polymeric, composite, plastic, or glass beads, matrices, boards or other shapes, including cylinders or tubes.

Analysis of the components of the sample mixture can be performed in one or more analytical trains. Analysis can comprise two-dimensional gel electrophoresis, one-dimensional gel electrophoresis, Western blotting, ELISA, protein or peptide mass fingerprinting, e.g., using MALDI-TOF/TOF, multidimensional electrophoresis, e.g., solution phase isoelectric focusing followed by two-dimensional gel electrophoresis of concentrated pI fractions, mass spectrometry (MALDI-MS, LC-MS/MS, MALDI-TOF MS, or LC-ESI-MS/MS), PCR, RT-PCR, and microarrays, thin-layer chromatography, liquid chromatography, e.g., HPLC, gas chromatography, GC/MS, electron microscopy, fluorescent microscopy, and surface analysis methods. In certain embodiments, isolated molecules or complexes thereof may be used in functional assays, e.g., enzymatic activity assays, in-vitro metabolism assays, etc., or subjected to subsequent fractionation or extraction steps.

Applications of the present disclosure can involve pressure-enhanced enzymatic digestion, e.g. proteolysis with trypsin, de-glycosylation with PHGase F (proteomics), removal of undesired protein by Proteinase K (genomics); sample preparation digestion for clinical proteomics, e.g. MRM assays for known biomarkers in plasma; chemical derivatization of samples for fluorescent detection, radio-isotope and stable isotope labeling; on-line cell lysis for drug metabolism studies, high-content screening and metabolomics; lysis of bacterial cells for detection of extreme pathogens (minimized hazardous sample handling; fully automated, unattended detection systems for field chemical or biological warfare or environmental monitoring; and automated point-of-care diagnostics).

The control system of the present disclosure may be implemented using one or more computer systems. The computer system may be, for example, a general-purpose computer such as those based on an Intel PENTIUM®-type processor, a Motorola PowerPC® processor, a Sun UltraSPARC® processor, a Hewlett-Packard PA-RISC® processor, or any other type of processor or combinations thereof. Alternatively, the computer system may include specially-programmed, special-purpose hardware, for example, an application-specific integrated circuit (ASIC) or controllers intended for analytical systems.

The computer system can include one or more processors typically connected to one or more memory devices, which can comprise, for example, any one or more of a disk drive memory, a flash memory device, a RAM memory device, or other device for storing data. The one or more memory devices can be used for storing programs and data during operation. For example, the one or more memory devices may be used for storing historical data relating to the parameters over a period of time, as well as operating data. Software, including programming code that implements embodiments of the disclosure, can be stored on a computer readable and/or writeable nonvolatile recording medium, and then typically copied into the one or more memory devices wherein it can then be executed by one or more processors. Such programming code may be written in any of a plurality of programming languages, for example, Labview, ladder logic, Java, Visual Basic, C, C#, or C++, Fortran, Pascal, Eiffel, Basic, COBOL, or any of a variety of combinations thereof.

Components of the control system may be coupled by an interconnection mechanism, which may include one or more busses, e.g., between components that are integrated within a same device and/or a network, e.g., between components that reside on separate discrete devices. The interconnection mechanism typically enables communications, e.g., data, instructions, to be exchanged between components of the control system.

The control system can also include one or more input devices, for example, a keyboard, mouse, trackball, microphone, touch screen, and one or more output devices, for example, a printing device, display screen, or speaker. In addition, the control system may contain one or more interfaces that can provide one or more indications or displays of the status or conditions of any of the various subsystems or components thereof. Such interfaces can be a man-machine display apparatus. Other components of the controller system provide connections to a communication network, in addition or as an alternative, to the network that may be formed by one or more of the components of the system.

According to one or more embodiments of the disclosure, the one or more input devices may include sensors for measuring parameters, such as a pressure transducer. The sensors, the metering valves and/or pumps, or all of these components may be connected to a communication network that is operatively coupled to the control system. For example, sensors that monitor a position or orientation of any of component or apparatus of the system, e.g., open or closed, may be configured as input devices that are directly connected to the control system. Metering valves, pumps, and motors, such as a pressure generator, may be configured as output devices that are connected to the control system, and any one or more of the above may be coupled to another computer system or component so as to communicate with the controller over a communication network. Such a configuration permits one sensor to be located at a significant distance from another sensor or allow any sensor to be located at a significant distance from any subsystem and/or the controller, while still providing data therebetween.

The control system can include one or more computer storage media such as readable and/or writeable nonvolatile recording medium in which signals can be stored that define a program to be executed by one or more processors. The medium may, for example, be a disk or flash memory. In typical operation, the one or more processors can cause data, such as code that implements one or more embodiments of the disclosure, to be read from the storage medium into a memory device that allows for faster access to the information by the one or more processors than does medium. The memory device is typically a volatile, random access memory such as a dynamic random access memory (DRAM) or static memory (SRAM) or other suitable devices that facilitates information transfer to and from the one or more processors.

The control system upon which various aspects of the disclosure may be practiced is not limited to being implemented in software, or on the controller. Indeed, rather than implemented on, for example, a general purpose computer system, the controller, or components or subsections thereof, may alternatively be implemented as a dedicated system or as a dedicated programmable logic controller (PLC) or in a distributed control system. Further, it should be appreciated that one or more features or aspects of the disclosure may be implemented in software, hardware or firmware, or any combination thereof. For example, one or more segments of an algorithm executable by the controller can be performed in separate computers, which in turn, can be communication through one or more networks.

The carrier body can be constructed from high strength materials. For example high strength precipitation strengthened stainless steel such as 15-5 or 17-4 would be good candidates. For very high pressure service, the inter-well offset can be doubled to 18 mm to allow sufficient material in between wells to withstand high pressure. When required, each pressurizing cell may be autofrettaged so as to impart a compressive residual stress to enhance fatigue resistance. Autofrettage may be achieved by direct over pressure of each chamber or by mechanical over-stress using a mandrel.

The yoke can also be constructed from high strength material. For example high strength precipitation strengthened stainless steel such as 15-5 or 17-4 may be utilized as the material of construction of the yoke. If low overall weight is a consideration, as in a mobile application, a titanium or wire wound yoke design may be used. Thus the present disclosure can be implemented as a portable, field deployable device contained in a portable housing as illustrated in FIG. 6.

For high cycle life applications, the yoke may include compressive residual stress to enhance fatigue resistance.

The microplate can be constructed from a material that has sufficient deformability and will not fracture under high hydrostatic pressure. Many polymers are suitable for this depending on the pressure and temperature used during processing. For example, because polyethylene has high flexibility, it can be suitable for most conditions that do not involve temperatures greater than 50° C. Other polymeric materials that can be considered include, for example, fluorinated ethylene propylene, which typically has high flexibility at all temperatures up to 120° C., and can withstand high pressure exposure; thermoplastic elastomers, which typically also have high elastic properties can also be used. Typically, the choice of material used for the microplate will be based on the final pressure, temperature, and chemical characteristics in service.

The encompassing configuration of the yoke also allows a secondary containment feature to be incorporated. If the control system detects a failure to seal the sample container, the volume contained within the yoke can be filled with a decontamination solution. The yoke can serve as a high thermal mass to allow stable temperature operation. Temperature controlling components can surround or be inserted within the yoke.

Having now described some illustrative embodiments of the disclosure, it should be apparent to those skilled in the art that the foregoing is merely illustrative and not limiting, having been presented by way of example only. Numerous modifications and other embodiments are within the scope of one of ordinary skill in the art and are contemplated as falling within the scope of the disclosure. In particular, although many of the examples presented herein involve specific combinations of method acts or system elements, it should be understood that those acts and those elements may be combined in other ways to accomplish the same objectives.

Those skilled in the art should appreciate that the parameters and configurations described herein are exemplary and that actual parameters and/or configurations will depend on the specific application in which the systems and techniques of the disclosure are used. Those skilled in the art should also recognize or be able to ascertain, using no more than routine experimentation, equivalents to the specific embodiments of the disclosure. It is therefore to be understood that the embodiments described herein are presented by way of example only and that, within the scope of the appended claims and equivalents thereto; the disclosure may be practiced otherwise than as specifically described.

Figure 8:
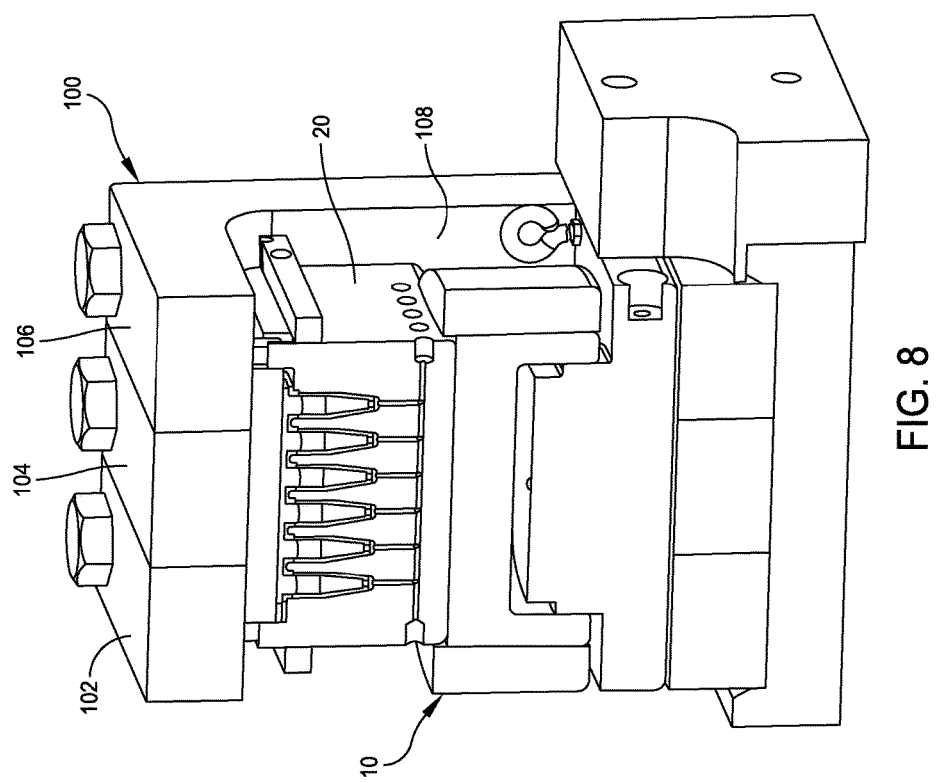
FIG. 8 is another schematic illustration showing a different perspective view of a portion of another embodiment of the sample pressurizing system which may be implemented in accordance with one or more aspects of the disclosure.

For example, FIG. 8 illustrates the sample pressurization system 10 received within a yoke, generally indicated at 100, of another embodiment of the disclosure. As shown, the yoke may be configured in several section, for example three yoke sections 102, 104, 106, to retain the components of the sample pressurizing system in place during one or more pressure cycles or pressurization events. The yoke 100 includes a casing cavity 108, which may be sized and configured to receive the carrier body 20 of the sample pressurization system 10.

In another embodiment, a chamber surrounding the yoke and the carrier can be filled with disinfecting reagent.

Moreover, it should also be appreciated that the disclosure is directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope of the disclosure as embodied in the claims. Further, acts, elements, and features discussed only in connection with one embodiment are not intended to be excluded from a similar role in other embodiments. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A sample pressurization device, comprising:
   a carrier body having at least one pressurizing fluid port, at least one fluid channel fluidly connected to the at least one pressurizing fluid port;
   at least one pressure cell defined by a cell cavity with an open end at a receiving surface of the carrier body, the at least one pressure cell being fluidly connectable to the at least one pressurizing fluid port through the at least one fluid channel;
   a pressure generator fluidly connected to the at least one pressurizing fluid port, the pressure generator configured to provide a pressurizing fluid in a range of about 10,000 psi to about 100,000 psi to the cell cavity;
   a microplate received on the receiving surface of the carrier body;
   at least one sample well included in the microplate, each sample well of the at least one sample well comprising a deformable material that deforms in response to an applied pressure from the pressurizing fluid such that, in operation, the at least one sample well deforms thereby transferring at least a portion of the applied pressure from the cell cavity to a sample contained within the at least one sample well, the at least one sample well being receivable in the at least one pressure cell, the microplate configured to fluidly isolate the sample in the at least one sample well from pressurizing fluid in the cell cavity, the at least one sample well sized to be at least partially contained within the cell cavity of the at least one pressure cell; and
   a capping plate disposed on the microplate.

2. The device of claim 1, wherein the at least one pressure cell has a retaining flange positioned circumferentially around the open end of the cell cavity at the receiving surface of the carrier body.

3. The device of claim 2, wherein the microplate has a planar surface and wherein the at least one sample well is at least partially defined by a sample well wall open at an end at the planar surface.

4. The device of claim 3, wherein the at least one sample well has a sealing flange circumferentially surrounding an outer perimeter of the sample well wall, at least a portion of the sealing flange being contiguous with at least a portion of the planar surface of the microplate.

5. The device of claim 4, wherein the sealing flange has a geometrical configuration corresponding with an inner geometrical configuration of the retaining flange.

6. The device of claim 2, wherein the capping plate comprises a planar cap surface and at least one cap projecting from the planar cap surface, the at least one cap having a geometrical configuration in complementary correspondence with an inner configuration of a capping section of the at least one sample well.

7. The device of claim 6, further comprising a loading plate configured to contact and distribute a second applied pressure onto the capping plate.

8. The device of claim 1, wherein the carrier body further comprises at least one foot with an actuatable ram, the foot having a pressure cavity defined between the actuatable ram and a footing section of the carrier body, the pressure cavity being fluidly connectable to a source of pressurizing fluid, and
   wherein the carrier body is disposed within a casing cavity of a yoke, and wherein the foot is configured to secure the carrier body within the yoke.

9. The device of claim 1, wherein the device is configured to subject the sample to pressure cycling.

10. The device of claim 1, further comprising a casing having an inner cavity sized and configured to receive the carrier body.

11. The device of claim 6, wherein the at least one cap is pierceable for sample retrieval.

12. The device of claim 1, wherein the at least one sample well comprises an elastic wall configured to transmit pressure from the cell cavity to an interior of the sample well.

13. The device of claim 1, wherein the at least one sample well is configured to sealingly enclose the sample from fluid communication with a pressurizing fluid in the cell cavity.

14. The device of claim 1, further comprising a clamp assembly that can be actuated to facilitate transfer of a force across the capping plate to the receiving surface of the carrier body.

15. The device of claim 14, further comprising an actuating fluid port connecting a pressure cavity within the clamp assembly to a source of a second pressurizing fluid capable of actuating the clamp assembly.

16. The device of claim 15, further comprising a loading plate configured to contact and distribute a second applied pressure onto the capping plate;
   wherein the actuating fluid port allows the second pressurizing fluid to be introduced into the pressure cavity to displace the carrier body and to secure the loading plate against an inner surface of a casing.

17. The device of claim 1, wherein the at least one sample well is a plurality of sample wells, and wherein the at least one pressure cell is a plurality of pressure cells, each one of the at least one sample well being receivable in a respective one of the at least one pressure cell.

* * * * *